US012630855B2

(12) United States Patent
Yoshida et al.

(10) Patent No.: US 12,630,855 B2
(45) Date of Patent: May 19, 2026

(54) POLYPEPTIDE HAVING ESTERIFICATION ACTIVITY FOR L-MENTHOL AND/OR HYDROLYZING ACTIVITY FOR L-MENTHOL ESTER

(71) Applicant: Amano Enzyme Inc., Nagoya (JP)

(72) Inventors: Kazunori Yoshida, Kakamigahara (JP); Yukihide Sato, Kakamigahara (JP); Tomoshi Kameda, Tokyo (JP); Jinzen Ikebe, Tokyo (JP)

(73) Assignee: Amano Enzyme Inc., Nagoya (JP)

( * ) Notice: Subject to any disclaimer, the term of this patent is extended or adjusted under 35 U.S.C. 154(b) by 636 days.

(21) Appl. No.: 17/906,217

(22) PCT Filed: Mar. 12, 2021

(86) PCT No.: PCT/JP2021/010072

§ 371 (c)(1),
(2) Date: Sep. 13, 2022

(87) PCT Pub. No.: WO2021/182611

PCT Pub. Date: Sep. 16, 2021

(65) Prior Publication Data

US 2024/0301463 A1 Sep. 12, 2024

(30) Foreign Application Priority Data

Mar. 13, 2020 (JP) ................................ 2020-044455

(51) Int. Cl.
*C12P 41/00* (2006.01)
*C12N 9/20* (2006.01)
*C12N 15/70* (2006.01)
*C12P 7/22* (2006.01)

(52) U.S. Cl.
CPC ............. *C12P 41/004* (2013.01); *C12N 9/20* (2013.01); *C12N 15/70* (2013.01); *C12P 7/22* (2013.01)

(58) Field of Classification Search
CPC . C12P 41/004; C12P 7/22; C12N 9/20; C12N 15/70; C12Y 301/01003; C40B 40/08; C40B 50/06
See application file for complete search history.

(56) References Cited

U.S. PATENT DOCUMENTS 7,314,739 B2 * 1/2008 Matuschek ............. C12N 9/20 435/320.1

FOREIGN PATENT DOCUMENTS

WO WO 2018/021324 A1 2/2018

OTHER PUBLICATIONS

Ema T, Fujii T, Ozaki M, Korenaga T, Sakai T. Rational control of enantioselectivity of lipase by site-directed mutagenesis based on the mechanism. Chemical communications. 2005(37):4650-1. (Year: 2005).*

Wahab RA, Basri M, Rahman RN, Salleh AB, Rahman MB, Leow TC. Facile modulation of enantioselectivity of thermophilic Geobacillus zalihae lipase by regulating hydrophobicity of its Q114 oxyanion. Enzyme and microbial technology. Nov. 1, 2016;93:174-81. (Year: 2016).*

Lafaquiere V, Barbe S, Puech-Guenot S, Guieysse D, Cortes J, Monsan P, Simeon T, Andre I, Remaud-Simeon M. Control of lipase enantioselectivity by engineering the substrate binding site and access channel. ChemBioChem. Nov. 23, 2009;10(17):2760-71. (Year: 2009).*

Livingstone CD, Barton GJ. Protein sequence alignments: a strategy for the hierarchical analysis of residue conservation. Bioinformatics. Dec. 1, 1993;9(6):745-56. (Year: 1993).*

Yang J, Koga Y, Nakano H, Yamane T. Modifying the chain-length selectivity of the lipase from Burkholderia cepacia KWI-56 through in vitro combinatorial mutagenesis in the substrate-binding site. Protein Engineering. Feb. 1, 2002;15(2):147-52. (Year: 2002).*

Extended European Search Report for European Application No. 27168659.1, dated Apr. 26, 2024, in 6 pages.

International Search Report in PCT/JP2021/010072 issued Apr. 13, 2021.

Ema, Tadashi et al., "Rational control of enantioselectivity of lipase by site-directed mutagenesis based on the mechanism", Chem. Commun., 2005, vol. 37, pp. 4650-4651.

Langrand, Georges et al., "Lipase Catalyzed Reactions and Strategy for Alcohol Resolution", Tetrahedron Letters, 1986, vol. 27, No. 1, pp. 29-32.

Wu, Wen-Hsin et al., "Lipase-catalyzed stereoselective esterification of DL-menthol in organic solvents using acid anhydrides as acylating agents", Enzyme and Microbial Technology, 1996, vol. 18, pp. 536-539.

Xu, J.-H. et al., "High-performance continuous operation for enantioselective esterification of menthol by use of acid anhydride and free lipase in organic solvent", Applied Microbiology and Biotechnology, 1995, vol. 43, Issue 4, pp. 639-643.

* cited by examiner

*Primary Examiner* — Jennifer M.H. Tichy
*Assistant Examiner* — Emily F Eix
(74) *Attorney, Agent, or Firm* — Knobbe, Martens, Olson & Bear, LLP

(57) ABSTRACT

Provided is a technique that can further improve substrate specificity to an L-form during L-menthol and/or L-menthol ester production. A polypeptide that: has A120G, Q88A, Q88G, Q88D, Q88M, Q88L variants of a polypeptide comprising the amino acid sequence represented by sequence no. 1, and in said variants, has a random different moiety other than an amino-acid residue into which a substitution has been introduced; has esterification activity for L-menthol and/or hydrolyzing activity for L-menthol ester, and improves substrate specificity to L-menthol and/or L-menthol ester compared to a polypeptide comprising the amino acid sequence represented by sequence no. 1. During L-menthol and/or L-menthol ester production, the polypeptide can further improve the optical purity of the product.

18 Claims, No Drawings

Specification includes a Sequence Listing.

POLYPEPTIDE HAVING ESTERIFICATION ACTIVITY FOR L-MENTHOL AND/OR HYDROLYZING ACTIVITY FOR L-MENTHOL ESTER

TECHNICAL FIELD

The present invention relates to a polypeptide having esterification activity for L-menthol and/or hydrolyzing activity for L-menthol ester. More specificity, the present invention relates to a polypeptide having esterification activity for L-menthol and/or hydrolyzing activity for L-menthol ester and having improved substrate specificity for L-menthol and/or L-menthol ester, a DNA encoding the polypeptide, a recombinant vector, a transformant, an enzyme composition, an enzyme preparation, a method for producing the polypeptide, and a method for producing L-menthol ester and a method for producing L-menthol that use the polypeptide.

REFERENCE TO SEQUENCE LISTING

The present application is being filed along with a Sequence Listing in electronic format. The Sequence Listing is provided as a file entitled 56280054_1.TXT, created and last modified on Sep. 13, 2022, which is 20.0 Kb in size. The information in the electronic format of the Sequence Listing is incorporated herein by reference in its entirety.

BACKGROUND ART

L-menthol is an important substance widely used in the perfume field, the food field, the pharmaceutical field, and the like because of its characteristics of exhibiting a refreshing flavor, a pleasant skin sensation, and the like. An ester of menthol serves as a raw material for L-menthol, and an ester of L-menthol itself is used in the perfume field, the food field, the pharmaceutical field, and the like.

These components are industrially produced by artificial synthesis. On the other hand, L-menthol and its ester obtained by synthesis are mixed with a D-form which is an optical isomer thereof. Both L-menthol and its ester are greatly affected by the incorporation of the D-form in their quality. Therefore, it is required to obtain L-menthol and its ester with a high optical purity.

Examples of a method for obtaining L-menthol and its ester in an optically selective manner include a chemical method and an enzymatic method. Examples of the chemical method include a method in which an optically active acid or base is reacted with DL-menthol to selectively crystallize an L-form. Examples of the enzymatic method include a method of specifically hydrolyzing the L-form by allowing a lipase to act on DL-menthol ester in an aqueous solvent, and a method of specifically esterifying the L-form by allowing a lipase to act on DL-menthol in an organic solvent.

Among them, various enzymatic methods have been studied from the viewpoint of a high degree of specificity of an enzyme. For example, Non-Patent Document 1 describes that a racemic menthyl laurate is hydrolyzed in an aqueous medium by a lipase derived from *Candida rugosa* to preferentially obtain L-menthol (ee: 70%). Such enantioselectivity is also recognized upon esterification of racemic menthol with lauric acid. For example, the lipase derived from *Candida rugosa* enantioselectively causes racemic menthol to undergo esterification with lauric acid in a non-aqueous medium to preferentially produce L-menthyl laurate (ee: 95%).

Non-Patent Document 2 describes that racemic menthol is esterified with acetic anhydride, propionic anhydride, and butyric anhydride in a specific enantioselectivity by a lipase derived from *Candida rugosa*, and particularly, L-menthyl butyrate is preferentially produced (ee: 86%) by esterification with butyric anhydride in n-hexane.

Non-Patent Document 3 describes that racemic menthol is esterified with propionic anhydride by a lipase derived from *Candida rugosa* to provide L-menthyl propionate having a very high optical purity (ee: 95%).

PRIOR ART DOCUMENTS

Non-Patent Documents

Non-Patent Document 1: Tetrahedron Letters, Vol. 27, No-1, pp 29-32, 1986

Non-Patent Document 2: Enzyme and Microbial Technology Volume 18, Issue 7, 1996, pp 536-539

Non-Patent Document 3: Applied Microbiology and Biotechnology. 1995, Volume 43, Issue 4, pp 639-643

SUMMARY OF THE INVENTION

Problems to be Solved by the Invention

However, there is still room for improvement in enantioselectivity obtained in production of L-menthol and/or its ester.

Therefore, an object of the present invention is to provide a technique that can further improve substrate specificity for an L-form in production of L-menthol and/or its ester.

Means for Solving the Problem

As a result of intensive studies, the present inventors have focused on a high degree of enantioselectivity of a lipase derived from *Burkholderia cepacia* and have further comprehensively examined the substrate specificity for the L-form in production of L-menthol and/or its ester for 840 or more kinds of lipase mutants obtained by introducing mutations into various sites of the lipase. As a result, the present inventors have found that a polypeptide comprising an amino acid sequence in which an amino acid residue at the 120th position of the lipase is substituted with a glycine residue and a polypeptide comprising an amino acid sequence in which an amino acid residue at the 88th position is substituted with an alanine residue, a glycine residue, an aspartic acid residue, a methionine residue, or a leucine residue can improve the substrate specificity for the L-form. The present invention has been completed based on this finding. That is, the present invention provides inventions of the following aspects.

Item 1. A polypeptide of any one of the following (1) to (3):

(1) a polypeptide comprising an amino acid sequence in which an amino acid residue at the 120th position is substituted with a glycine residue in an amino acid sequence shown in SEQ ID NO: 1;

(2) a polypeptide comprising an amino acid sequence in which an amino acid residue at the 120th position is substituted with a glycine residue in an amino acid sequence shown in SEQ ID NO: 1, and one or a few amino acid residues other than the amino acid residue introduced by the substitution are substituted, added, inserted, or deleted, having esterification activity for L-menthol and/or hydrolyzing activity for L-menthol ester, and having improved substrate specificity for L-menthol and/or L-menthol ester as compared with a polypeptide comprising an amino acid sequence shown in SEQ ID NO: 1; and (3) a polypeptide comprising an amino acid sequence in which an amino acid residue at the 120th position is substituted with a glycine residue in an amino acid sequence shown in SEQ ID NO: 1, having 80% or more sequence identity to an amino acid sequence shown in SEQ ID NO: 1 except for the amino acid residue introduced by the substitution, having esterification activity for L-menthol and/or hydrolyzing activity for L-menthol ester, and having improved substrate specificity for L-menthol and/or L-menthol ester as compared with a polypeptide comprising an amino acid sequence shown in SEQ ID NO: 1.

Item 2. A polypeptide of any one of the following (4) to (6):

(4) a polypeptide comprising an amino acid sequence in which an amino acid residue at the 88th position is substituted with an alanine residue, a glycine residue, an aspartic acid residue, a methionine residue, or a leucine residue in an amino acid sequence shown in SEQ ID NO: 1;

(5) a polypeptide comprising an amino acid sequence in which an amino acid residue at the 88th position is substituted with an alanine residue, a glycine residue, an aspartic acid residue, a methionine residue, or a leucine residue in an amino acid sequence shown in SEQ ID NO: 1, and one or a few amino acid residues other than the amino acid residue introduced by the substitution are substituted, added, inserted, or deleted, having esterification activity for L-menthol and/or hydrolyzing activity for L-menthol ester, and having improved substrate specificity for L-menthol and/or L-menthol ester as compared with a polypeptide comprising an amino acid sequence shown in SEQ ID NO: 1; and (6) a polypeptide comprising an amino acid sequence in which an amino acid residue at the 88th position is substituted with an alanine residue, a glycine residue, an aspartic acid residue, a methionine residue, or a leucine residue in an amino acid sequence shown in SEQ ID NO: 1, having 80% or more sequence identity to an amino acid sequence shown in SEQ ID NO: 1 except for the amino acid residue introduced by the substitution, having esterification activity for L-menthol and/or hydrolyzing activity for L-menthol ester, and having improved substrate specificity for L-menthol and/or L-menthol ester as compared with a polypeptide comprising an amino acid sequence shown in SEQ ID NO: 1.

Item 3. A DNA encoding the polypeptide described in Item 1 or 2.

Item 4. A recombinant vector comprising the DNA described in Item 3.

Item 5. A transformant obtained by transforming a host with the recombinant vector described in Item 4.

Item 6. A method for producing the polypeptide described in Item 1 or 2, the method comprising a step of culturing the transformant described in Item 5.

Item 7. An enzyme composition comprising the polypeptide described in Item 1 or 2.

Item 8. An enzyme preparation comprising the polypeptide described in Item 1 or 2 or the enzyme composition described in Item 7.

Item 9. A method for producing L-menthol ester, the method comprising a step of esterifying L-menthol by allowing the polypeptide described in Item 1 or 2, the enzyme composition described in Item 7, or the enzyme preparation described in Item 8 to act on a mixture containing L-menthol and D-menthol.

Item 10. A method for producing L-menthol, the method comprising a step of hydrolyzing L-menthol ester by allowing the polypeptide described in Item 1 or 2, the enzyme composition described in Item 7, or the enzyme preparation described in Item 8 to act on a mixture containing L-menthol ester and D-menthol ester.

Advantages of the Invention

According to the present invention, there is provided a technique that can further improve substrate specificity for an L-form in production of L-menthol and/or its ester.

EMBODIMENTS OF THE INVENTION

Hereinafter, the present invention will be described in detail. 20 amino acid residues in amino acid sequences excluding the sequence lists may be abbreviated as one-letter codes. That is, glycine (Gly) is G, alanine (Ala) is A, valine (Val) is V, leucine (Leu) is L, isoleucine (Ile) is I, phenylalanine (Phe) is F, tyrosine (Tyr) is Y, tryptophan (Trp) is W, serine (Ser) is S, treonine (Thr) is T, cysteine (Cys) is C, methionine (Met) is M, aspartic acid (Asp) is D, glutamic acid (Glu) is E, asparagine (Asn) is N, glutamine (Gln) is Q, lysine (Lys) is K, arginine (Arg) is R, histidine (His) is H, and proline (Pro) is P.

In the present specification, the amino acid sequence to be displayed is N-terminal at the left end and C-terminal at the right end.

In the present specification, expression such as "A120G" is a notation of amino acid substitution. For example, "A120G" means that the 120th amino acid A from the N-terminal side in the specific amino acid sequence is substituted with an amino acid G.

In the present specification, the term "non-polar amino acid" includes alanine, valine, leucine, isoleucine, proline, methionine, phenylalanine, and tryptophan. The term "non-charged amino acid" includes glycine, serine, threonine, cysteine, tyrosine, asparagine, and glutamine. The term "acidic amino acid" includes aspartic acid and glutamic acid. The term "basic amino acid" includes lysine, arginine, and histidine.

In the present specification, the term "substitution" includes not only a case where a substitution of an amino acid residue is artificially introduced, but also a case where a substitution of an amino acid residue is naturally introduced, that is, a case where amino acid residues are originally different. In the present specification, the substitution of an amino acid residue may be an artificial substitution or a natural substitution, but an artificial substitution is preferred.

1. Polypeptide

A polypeptide of the present invention is a polypeptide as shown in any one of the following (1) to (3) or a polypeptide as shown in any one of the following (4) to (6).

(1) A polypeptide comprising an amino acid sequence in which an amino acid residue (alanine residue) at the 120th position is substituted with a glycine residue in an amino acid sequence shown in SEQ ID NO: 1, (2) a polypeptide comprising an amino acid sequence in which an amino acid residue at the 120th position is substituted with a glycine residue in an amino acid sequence shown in SEQ ID NO: 1, and one or a few amino acid residues other than the amino acid residue introduced by the substitution are substituted, added, inserted, or deleted, having esterification activity for L-menthol and/or hydrolyzing activity for L-menthol ester, and having improved substrate specificity for L-menthol and/or L-menthol ester as compared with a polypeptide comprising an amino acid sequence shown in SEQ ID NO: 1, and (3) a polypeptide comprising an amino acid sequence in which an amino acid residue at the 120th position is substituted with a glycine residue in an amino acid sequence shown in SEQ ID NO: 1, having 80% or more sequence identity to an amino acid sequence shown in SEQ ID NO: 1 except for the amino acid residue introduced by the substitution, having esterification activity for L-menthol and/or hydrolyzing activity for L-menthol ester, and having improved substrate specificity for L-menthol and/or L-menthol ester as compared with a polypeptide comprising an amino acid sequence shown in SEQ ID NO: 1.

(4) A polypeptide comprising an amino acid sequence in which an amino acid residue (glutamine residue) at the 88th position is substituted with an alanine residue, a glycine residue, an aspartic acid residue, a methionine residue, or a leucine residue in an amino acid sequence shown in SEQ ID NO: 1, (5) a polypeptide comprising an amino acid sequence in which an amino acid residue at the 88th position is substituted with an alanine residue, a glycine residue, an aspartic acid residue, a methionine residue, or a leucine residue in an amino acid sequence shown in SEQ ID NO: 1, and one or a few amino acid residues other than the amino acid residue introduced by the substitution are substituted, added, inserted, or deleted, having esterification activity for L-menthol and/or hydrolyzing activity for L-menthol ester, and having improved substrate specificity for L-menthol and/or L-menthol ester as compared with a polypeptide comprising an amino acid sequence shown in SEQ ID NO: 1, and (6) a polypeptide comprising an amino acid sequence in which an amino acid residue at the 88th position is substituted with an alanine residue, a glycine residue, an aspartic acid residue, a methionine residue, or a leucine residue in an amino acid sequence shown in SEQ ID NO: 1, having 80% or more sequence identity to an amino acid sequence shown in SEQ ID NO: 1 except for the amino acid residue introduced by the substitution, having esterification activity for L-menthol and/or hydrolyzing activity for L-menthol ester, and having improved substrate specificity for L-menthol and/or L-menthol ester as compared with a polypeptide comprising an amino acid sequence shown in SEQ ID NO: 1.

The polypeptides shown in (1) to (6) have esterification activity for L-menthol and/or hydrolyzing activity for L-menthol ester, and have improved substrate specificity for L-menthol and/or L-menthol ester. Preferably, the polypeptides shown in (1) to (6) have improved substrate specificity for L-menthol and L-menthol ester.

The polypeptide of SEQ ID NO: 1 is a wild-type lipase (mature form) derived from *Burkholderia cepacia.*

The polypeptides of (1) to (6) include not only polypeptides obtained by artificial substitution but also polypeptides originally having such an amino acid sequence.

The polypeptide of (1) and the polypeptide (4) also include polypeptides containing both a substitution at the 120th position and a substitution at the 88th position.

Hereinafter, in the polypeptides of (2) and (3) and the polypeptides of (5) and (6), amino acid residues other than the amino acid residue at the 120th position or the amino acid residue at the 88th position of SEQ ID NO: 1 may be referred to "arbitrary difference sites". In the present specification, the term "arbitrary difference site" is a site at which a difference is allowed as long as it does not significantly affect the properties of the polypeptide. In the present specification, a polypeptide having a difference in the amino acid sequence at an arbitrary difference site as compared to the polypeptide of (1) or (4) but having substrate specificity for L-menthol and/or L-menthol ester that is comparable with or higher than that of the polypeptide of (1) or (4) is referred to as a variant of the polypeptide of (1) or (4). It is preferable that the variant of the polypeptide has a difference in the amino acid sequence at an arbitrary difference site as compared to the polypeptide of (1) or (4) but has substantially the same properties of the polypeptide. The expression "substantially the same" refers to having substrate specificity for L-menthol and/or L-menthol ester. The polypeptides of (2) and (3) are variants of the polypeptide of (1), and the polypeptides of (5) and (6) are variants of the polypeptide of (4).

The amino acid differences in the polypeptide of (2) and (5) may comprise only one of the differences (for example, substitution) including substitution, addition, insertion, and deletion or comprise two or more of the differences (for example, substitution and insertion). The number of amino acid differences at an arbitrary difference site in the polypeptides of (2) and (5) may be 1 or several, and is, for example, 1 to 50, preferably 1 to 20, 1 to 10, 1 to 8, 1 to 7, 1 to 6, 1 to 5, or 1 to 4, further preferably 1 to 3, and particularly preferably 1 or 2, or 1.

In the polypeptides of (2) and (5), the sequence identity to each amino acid sequence shown in SEQ ID NO: 1 except for the site at which the amino acid substitution has been made may be 80% or more, but is preferably 85% or more or 90% or more, further preferably 95% or more, 96% or more, 97% or more, or 98% or more, and particularly preferably 99% or more.

In the polypeptides of (3) and (6), the sequence identity to each amino acid sequence shown in SEQ ID NO: 1 except for the site at which the amino acid substitution has been made is a sequence identity calculated by extracting only the arbitrary difference site from each amino acid sequence shown in SEQ ID NO: 1 and comparing only the arbitrary difference site. The "sequence identity" refers to a value of amino acid sequence identity obtained by bl2seq program (Tatiana A. Tatsusova, Thomas L. Madden, FEMS Microbiol. Lett., Vol. 174, p 247-250, 1999) in BLAST PACKAGE [sgi32 bit edition, Version 2.0.12; available from National Center for Biotechnology Information (NCBI)]. Parameter settings may be as follows: Gap insertion Cost value: 11 and Gap extension Cost value: 1.

In the polypeptides of (2), (3), (5), and (6), the amino acids at the 87th position (serine), the 264th position (aspartic acid), and the 286th position (histidine) in the amino acid sequence shown in SEQ ID NO: 1 are considered to contribute to esterification activity for L-menthol and/or hydrolyzing activity for L-menthol ester, and thus it is desirable not to introduce substitutions or deletions at these sites.

When an amino acid substitution is introduced into the polypeptides of (2), (3), (5), and (6), a conservative substitution is mentioned as an aspect of the amino acid substitution. That is, examples of the amino acid substitution introduced into the amino acid sequence shown in SEQ ID NO: 1 in the polypeptides of (2), (3), (5), and (6) include the following substitutions: when an amino acid to be substituted is a non-polar amino acid, a substitution with other non-polar amino acids; when an amino acid to be substituted is a non-charged amino acid, a substitution with other non-charged amino acids; when an amino acid to be substituted is an acidic amino acid, a substitution with other acidic amino acids; and when an amino acid to be substituted is a basic amino acid, a substitution with other basic amino acids.

In the polypeptides of (2), (3), (5), and (6), "a polypeptide having esterification activity for L-menthol and/or hydrolyzing activity for L-menthol ester, and having improved substrate specificity for L-menthol and/or L-menthol ester as compared with a polypeptide comprising an amino acid sequence shown in SEQ ID NO: 1" means (i) having esterification activity for L-menthol and/or hydrolyzing activity for L-menthol ester and (ii-a) regarding substrate specificity for L-menthol, the optical purity of L-menthol acetyl ester as measured under the conditions of Test Example 2 below being 1.007 times or more, preferably 1.009 times or more, more preferably 1.010 times or more, and further preferably 1.012 times or more the optical purity of a polypeptide comprising an amino acid sequence shown in SEQ ID NO: 1 (provided that, when the L-menthol ester conversion rates in the polypeptide of the present invention and the polypeptide comprising an amino acid sequence shown in SEQ ID NO: 1 are the same, specifically, 99 to 101%), and means (ii-b) regarding substrate specificity for L-menthol ester, the ratio of the conversion rate to L-menthol to the conversion rate to D-menthol (L/D conversion rate) as measured under the conditions of Test Example 1 being 1.05 times or more, preferably 1.12 times or more, more preferably 1.19 times or more, further preferably 1.26 times or more, and even more preferably 1.32 times or more the L/D conversion rate of a polypeptide comprising an amino acid sequence shown in SEQ ID NO: 1.

2. DNA

A DNA encoding the polypeptide of the present invention (hereinafter, also described as "DNA of the present invention" in some cases) can be obtained, for example, by introducing the amino acid mutation into a DNA encoding an amino acid sequence (SEQ ID NO: 1) of a wild-type lipase. The DNA of the present invention can also be artificially synthesized by a total gene synthesis method.

The DNA encoding a polypeptide comprising an amino acid sequence shown in SEQ ID NO: 1 is known as, for example, a nucleotide sequence shown SEQ ID NO: 2, and can be isolated from the genomic DNA of the M-12-33 strain of *Burkholderia cepacia* by a conventional method using PCR.

The method for introducing a specific mutation into a specific site of a nucleotide sequence is well-known, and for example, a site-specific mutagenesis introduction method of DNA or the like can be used. Examples of a specific method of converting a base in a DNA include a method using a commercially available kit (such as QuickChange Lightning Site-Directed Mutagenesis kit: manufactured by Stratagene or KOD-Plus-Mutagenesis kit: manufactured by TOYOBO CO., LTD.).

The nucleotide sequence of the DNA into which a mutation has been introduced can be confirmed using a DNA sequencer. The nucleotide sequence is determined once, and thereafter, the DNA encoding the polypeptide can be obtained by chemical synthesis, PCR using a cloned probe as a template, or hybridization using a DNA fragment having the nucleotide sequence as a probe.

It is possible to synthesize a mutant form of DNA encoding the peptide, which has a function equivalent to that before mutation, by site-directed mutagenesis or the like. In order to introduce a mutation into the DNA encoding the peptide, a known method such as a Kunkel method, a Gapped duplex method, or a megaprimer PCR method can be used.

The DNA of the present invention is preferably a DNA in which the codon usage frequency is optimized for the host, and more preferably a DNA in which the codon usage frequency is optimized for *Escherichia coli.*

As an index representing the codon usage frequency, the total host optimal codon usage frequency of each codon may be adopted. The optimal codon is defined as a codon having the highest usage frequency among codons corresponding to the same amino acid. The codon usage frequency is not particularly limited as long as it is optimized for the host, and examples of the optimal codon for *Escherichia coli* include the following. F: phenylalanine (ttt), L: leucine (ctg), I: isoleucine (att), M: methionine (atg), V: valine (gtg), Y: tyrosine (tat), stop codon (taa), H: histidine (cat), Q: glutamine (cag), N: asparagine (aat), K: lysine (aaa), D: aspartic acid (gat), E: glutamic acid (gaa), S: serine (agc), P: proline (ccg), T: threonine (acc), A: alanine (gcg), C: cysteine (tgc), W: tryptophan (tgg), R: arginine (cgc), G: glycine (ggc).

Examples of the DNA of the present invention include DNAs comprising nucleotide sequences shown in SEQ ID NOs: 3 and 13 to 17. The DNA comprising a nucleotide sequence shown in SEQ ID NO: 3 encodes a polypeptide in which the 120th position of the amino acid sequence of the polypeptide shown in SEQ ID NO: 1 described in the above (1) is substituted with a glycine residue. Each of the DNAs comprising nucleotide sequences shown in SEQ ID NOs: 13, 14, 15, 16, and 17 encodes a polypeptide in which the amino acid residue at the 88th position of the amino acid sequence of the polypeptide shown in SEQ ID NO: 1 described in the above (4) is substituted with an alanine residue, a glycine residue, an aspartic acid residue, a methionine residue, and a leucine residue.

Other examples of the DNA of the present invention include DNAs encoding a polypeptide having improved substrate specificity for L-menthol and/or L-menthol ester as compared with a polypeptide comprising an amino acid sequence shown in SEQ ID NO: 1, and hybridizing, under stringent conditions, with a DNA comprising a nucleotide sequence that is complementary to DNAs comprising nucleotide sequences shown in SEQ ID NOs: 3 and 13 to 17.

Here, the expression "under stringent conditions" refers to conditions of incubating in 6×SSC (1×SSC is 0.15 M NaCl, 0.015 M sodium citrate, pH 7.0) containing 0.5% SDS, 5×Denhartz's [Denhartz's, 0.1% bovine serum albumin (BSA), 0.1% polyvinylpyrrolidone, 0.1% Ficoll 400], and 100 μg/ml of a salmon sperm DNA at 50° C. to 65° C. for 4 hours to overnight.

The hybridization under stringent conditions is specifically performed by the following method. That is, a nylon membrane on which a DNA library or a cDNA library is immobilized is prepared, and the nylon membrane is blocked at 65° C. in a prehybridization solution containing 6×SSC, 0.5% SDS, 5×Denhartz's, and 100 μg/ml of a salmon sperm DNA. Thereafter, each probe labeled with $^{32}P$ is added and incubated at 65° C. overnight. This nylon membrane is washed in 6×SSC at room temperature for 10 minutes, in 2×SSC containing 0.1% SDS at room temperature for 10 minutes, and in 0.2×SSC containing 0.1% SDS at 45° C. for 30 minutes, then autoradiography is performed, and a DNA specifically hybridized with the probe can be detected.

Further examples of the DNA of the present invention include DNAs encoding a polypeptide having improved substrate specificity for L-menthol and/or L-menthol ester as compared with a polypeptide comprising an amino acid sequence shown in SEQ ID NO: 1 and having 80% or more homology of DNAs comprising nucleotide sequences shown in SEQ ID NOs: 3 and 13 to 17. The homology is preferably 85% or more or 90% or more, further preferably 95% or more, 96% or more, or 97% or more, and particularly preferably 98% or more or 99% or more.

Here, the "homology" of DNA is calculated using a disclosed or commercially available software with an algorithm that makes a comparison using the standard sequence as a reference sequence. Specifically, BLAST, FASTA, GENETYX (manufactured by Software Development Co., Ltd), or the like can be used, and these may be used with default parameters being set.

3. Recombinant Vector

A recombinant vector comprising the DNA encoding the peptide of the present invention (hereinafter, also described as "recombinant vector of the present invention" in some cases) can be obtained by inserting the DNA of the present invention into an expression vector.

The recombinant vector of the present invention includes a control factor such as a promoter operably linked to the DNA of the present invention. Typical examples of the control factor include a promoter, but the control factor may further include transcription elements such as an enhancer, a CCAAT box, a TATA box, and an SPI site, as necessary. The expression "operably linked" means that various control factors such as a promoter and an enhancer that control the DNA of the present invention are linked to the DNA of the present invention in a state of being capable of operating in a host cell.

As the expression vector, those constructed for recombination from phage, plasmid, or virus capable of autonomously growing in the host are suitable. Such expression vectors are well-known, and examples of a commercially available expression vector include pQE vector (QIAGEN GmbH), pDR540 and pRIT2T (GE Healthcare Bio-Sciences KK), and pET vector (Merck KGaA, Darmstadt, Germany). The expression vector may be used by selecting an appropriate combination with a host cell, and for example, in the case of using *Escherichia coli* as a host cell, a combination of the pET vector and an *Escherichia coli* strain DH5a, a combination of the pET vector and an *Escherichia coli* strain BL21 (DE3), a combination of the pDR540 vector and an *Escherichia coli* strain JM109, or the like is preferably mentioned.

4. Transformant

A transformant (hereinafter, also described as "transformant of the present invention" in some cases) is obtained by transforming a host with the recombinant vector of the present invention.

The host used for the production of the transformant is not particularly limited as long as the recombinant vector is stable, capable of autonomous growth, and capable of expressing a trait of an exogenous gene, but for example, bacteria belonging to the genus of *Escherichia* such as *Escherichia coli*, the genus of *Bacillus* such as *Bacillus subtilis*, and the genus of *Pseudomonas* such as *Pseudomonas putida*; yeasts, and the like are preferably exemplified, and other than, the host may be an animal cells, an insect cell, a plant, and the like. Among these, *Escherichia coli* is particularly preferred.

The transformant of the present invention can be obtained by introducing the recombinant vector of the present invention into a host, and conditions for introducing the recombinant vector into the host may be appropriately set according to the type of the host and the like. When the host is a bacterium, for example, a method using a competent cell by a calcium ion treatment, an electroporation method, and the like are mentioned. When the host is a yeast, for example, an electroporation method, a spheroplast method, a lithium acetate method, and the like are mentioned. When the host is an animal cell, for example, an electroporation method, a calcium phosphate method, a lipofection method, and the like are mentioned. When the host is an insect cell, for example, a calcium phosphate method, a lipofection method, an electroporation method, and the like are mentioned. When the host is a plant cell, for example, an electroporation method, an *Agrobacterium* method, a particle gun method, a PEG method, and the like are mentioned.

Whether or not the recombinant vector of the present invention has been incorporated into a host can be confirmed by a PCR method, a Southern hybridization method, a Northern hybridization method, and the like.

When it is confirmed whether or not the recombinant vector of the present invention has been incorporated into a host by a PCR method, for example, the recombinant vector may be separated and purified from a transformant.

For example, when the host is a bacterium, the separation and purification of the recombinant vector are performed based on a lysate obtained by lysing the bacterium. As a lysis method, for example, a treatment is performed with a lytic enzyme such as lysozyme, and as necessary, a protease, other enzymes, and a surfactant such as sodium lauryl sulfate (SDS) are used in combination.

Physical crushing methods such as freeze thawing and French press processing may be combined. The separation and purification of a DNA from a lysate can be performed, for example, by appropriately combining a deproteinization treatment using a phenol treatment and a protease treatment, a ribonuclease treatment, an alcohol precipitation treatment, and a commercially available kit.

DNA cleavage can be performed according to a conventional method, for example, using a restriction enzyme treatment. As a restriction enzyme, for example, a type II restriction enzyme that acts on a specific nucleotide sequence is used. Binding between the DNA and the expression vector is performed, for example, using a DNA ligase.

Thereafter, PCR is performed by designing a primer specific to the DNA of the present invention using the separated and purified DNA as a template. The amplification product obtained by PCR is subjected to agarose gel electrophoresis, polyacrylamide gel electrophoresis, capillary electrophoresis, or the like, and is stained with ethidium bromide, SYBR Green solution, and the like, and then the amplification product is detected as a band, so that transformation can be confirmed.

PCR can be performed using a primer labeled with a fluorescent dye or the like in advance to detect an amplification product. A method of binding an amplification product to a solid phase such as a microplate and confirming the amplification product by fluorescence, an enzyme reaction, or the like may also be adopted.

5. Method for Producing Polypeptide

The polypeptide of the present invention can be obtained by a production method including a step of culturing the transformant of the present invention.

The culture conditions of the transformant may be appropriately set in consideration of the nutritional physiological properties of the host, and liquid culture is preferably mentioned. In the case of performing industrial production, ventilating/stirring culture is preferred.

As a nutrient source of the medium, those required for growth of transformants can be used. A carbon source may be any assimilable carbon compound, and examples thereof include glucose, sucrose, lactose, maltose, molasses, and pyruvic acid.

A nitrogen source may be any assimilable nitrogen compound, and examples thereof include peptone, meat extract, yeast extract, casein hydrolysate, and soybean cake alkaline extract.

In addition to the carbon source and the nitrogen source, for example, phosphates, carbonates, sulfates, salts of magnesium, calcium, potassium, iron, manganese, zinc, and the like, specific amino acids, specific vitamins, and the like may be used as necessary.

The culture temperature can be appropriately set in a range in which the transformant of the present invention can grow and the transformant of the present invention produces the polypeptide of the present invention, but is preferably about 15 to 37° C. The culturing may be completed at an appropriate time with reference to the time when the polypeptide of the present invention reaches the highest yield, and the culturing time is usually about 12 to 48 hours.

The transformant of the present invention is cultured, the culture solution is collected by a method such as centrifugation to recover a supernatant or bacterial cells, the bacterial cells are treated by a mechanical method such as ultrasonic wave and French press or a lytic enzyme such as lysozyme, and as necessary, are solubilized by using an enzyme such as protease or a surfactant such as sodium lauryl sulfate (SDS), whereby a water-soluble fraction containing the polypeptide of the present invention can be obtained.

By selecting an appropriate expression vector and host, the expressed polypeptide of the present invention can also be secreted into the culture solution.

The water-soluble fraction containing the polypeptide of the present invention obtained as described above may be subjected to a purification treatment as it is, or may be subjected to a purification treatment after the polypeptide of the present invention in the water-soluble fraction is concentrated.

The concentration can be performed by, for example, concentration under reduced pressure, membrane concentration, a salting-out treatment, fractionation precipitation with a hydrophilic organic solvent (for example, methanol, ethanol, and acetone), or the like.

The purification treatment of the polypeptide of the present invention can be performed, for example, by appropriately combining methods such as gel filtration, adsorption chromatography, ion exchange chromatography, and affinity chromatography.

The purification treatment is already known, and can proceed by referring to appropriate documents, magazines, textbooks, and the like. The polypeptide of the present invention thus purified can be pulverized by freeze drying, vacuum drying, spray drying, or the like, as necessary, and then distributed to the market.

6. Enzyme Composition

The polypeptide of the present invention may be provided, for example, in the form of a composition in which other components coexist. Examples of the form of the enzyme composition include a culture solution containing the polypeptide obtained in the process of producing the polypeptide of the present invention, a water-soluble fraction containing the polypeptide obtained from the culture solution, or a composition obtained by increasing the purification degree of the polypeptide to an arbitrary level from the water-soluble fraction; an enzyme preparation shown in "7. Enzyme preparation" below; and a reaction mixture containing the unreacted polypeptide obtained by using the polypeptide of the present invention for production of L-menthol and/or its ester.

Examples of other components contained in the enzyme composition include optional components added, produced, or mixed in the preparation process of the enzyme composition, and for example, contaminant protein components and/or components other than proteins derived from the medium used for the production of the polypeptide of the present invention; additives or bases shown in "7. Enzyme preparation" below; unreacted raw materials and products contained in the reaction mixture obtained in the production of L-menthol and/or its ester, and the like are mentioned.

The enzyme composition may also contain other enzymes. Examples of the other enzymes include amylase (α-amylase, β-amylase, or glucoamylase), glucosidase (α-glucosidase or β-glucosidase), galactosidase (α-galactosidase or β-galactosidase), protease (acidic protease, neutral protease, or alkaline protease), peptidase (leucine peptidase or aminopeptidase), lipase, esterase, cellulase, phosphatase (acid phosphatase or alkaline phosphatase), nuclease, deaminase, oxidase, dehydrogenase, glutaminase, pectinase, catalase, dextranase, transglutaminase, protein deamidase, and pullulanase.

The content of the polypeptide of the present invention in the enzyme composition is not particularly limited, but is preferably 10 mass % or more and more preferably 30 mass % or more in the total protein of the enzyme composition. The form of the enzyme composition is not particularly limited, and examples thereof include liquids, powders, and granules. The enzyme composition can be prepared by a generally known method or a method shown in "8-3. Method for producing L-menthol ester" below.

7. Enzyme Preparation

The polypeptide of the present invention or the enzyme composition containing the polypeptide of the present invention may be provided, for example, in the form of an enzyme preparation. The enzyme preparation is an enzyme composition prepared for the purpose of using the polypeptide of the present invention in "8. Use application" described below, and contains the polypeptide of the present invention as an active ingredient. The enzyme preparation may contain an additive such as an excipient, a buffer agent, a suspending agent, a stabilizer, a preservative, an antiseptic, saline, or a solvent, or a base besides the polypeptide of the present invention. As the excipient, starch, dextrin, maltose, trehalose, lactose, D-glucose, sorbitol, D-mannitol, sucrose, glycerol, and the like can be used. As the buffer agent, phosphate, citrate, acetate, and the like can be used. As the stabilizer, propylene glycol, ascorbic acid, and the like can be used. As the preservative, phenol, benzalkonium chloride, benzyl alcohol, chlorobutanol, methylparaben, and the like can be used. As the antiseptic, ethanol, benzalkonium chloride, paraoxybenzoic acid, chlorobutanol, and the like can be used. The enzyme preparation may contain other components (for example, any component and the like added, produced, or mixed in the production process of the polypeptide as an active ingredient) to the extent that the effect of the present invention is not affected. The content of the polypeptide in the enzyme preparation is appropriately set in a range in which the effect of the polypeptide is exhibited.

8. Use Application

The polypeptide of the present invention can be used for use applications requiring an esterification treatment for L-menthol, and a hydrolysis treatment for L-menthol ester. Examples of the use applications requiring an esterification treatment for L-menthol include production of L-menthol ester, and examples of the use applications requiring a hydrolysis treatment for L-menthol ester include production of L-menthol. More specific examples of these use applications include production of a perfume compound; production of an additive of food and drink, a cosmetic, a pharmaceutical, or a quasi-pharmaceutical product; production of an active ingredient of a cosmetic, a pharmaceutical, or a quasi-pharmaceutical product; and production of an intermediate of an active ingredient of a cosmetic, a pharmaceutical, or a quasi-pharmaceutical product.

8-1. Substrate

L-menthol and/or L-menthol ester as a substrate of the polypeptide of the present invention is well-known as a perfume compound; an additive of food and drink, a cosmetic, a pharmaceutical, or a quasi-pharmaceutical product; an active ingredient of a cosmetic, a pharmaceutical, or a quasi-pharmaceutical product; an intermediate of an active ingredient of a cosmetic, a pharmaceutical, or a quasi-pharmaceutical product; or the like.

L-menthol is (1R,2S,5R)-5-methyl-2-(1-ethylethyl)cyclohexanol. L-menthol ester is not particularly limited as long as it is an ester of L-menthol and a carboxylic acid, and specific examples thereof include a compound represented by the following Formula (1).

[Chemical Formula 1]

(1)

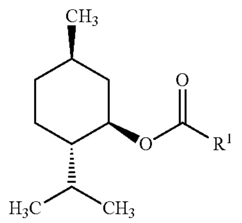

In Formula (1), $R^1$ represents a linear or branched alkyl group having 1 to 20 carbon atoms, preferably 1 to 6 carbon atoms, a cycloalkyl group having 3 to 8 carbon atoms, an aryl group having 6 to 14 carbon atoms, an aralkyl group having 7 to 15 carbon atoms, an alkoxy group having 1 to 20 carbon atoms, or an alkylamino group having 1 to 20 carbon atoms. The alkyl group, the cycloalkyl group, the aryl group, the aralkyl group, the alkyl group of the alkoxy group, and the alkyl group of the alkylamino group may be unsubstituted or substituted, and examples of a substituent in the case of being substituted include a hydroxyl group, a formyl group, an alkoxy group having 1 to 6 carbon atoms, a carboxyl group, a mercapto group, a sulfo group, an amino group, an alkylamino group having 1 to 6 carbon atoms, a nitro group, and a halogen group.

Preferred examples of L-menthol ester include L-menthyl acetate, L-menthyl benzoate, L-menthyl isovalerate, L-menthyl lactate, L-menthyl succinate, L-menthyl propionate, and L-menthyl butyrate, and L-menthyl acetate is preferably mentioned.

8-2. Mode of Use of Polypeptide

The usage form of the polypeptide of the present invention is not particularly limited, and examples thereof include a free polypeptide form and an immobilized polypeptide form. The immobilized polypeptide may be obtained by immobilizing the polypeptide of the present invention on a carrier (for example, an ion exchange resin, a porous resin, ceramics, calcium carbonate, or the like) according to a conventional method.

The polypeptide of the present invention may be used singly or in combination of a plurality of kinds thereof.

8-3. Method for Producing L-Menthol Ester

A method for producing L-menthol ester of the present invention includes a step of esterifying L-menthol by allowing the polypeptide of the present invention, the enzyme composition of the present invention, or the enzyme preparation of the present invention (hereinafter, described as “the polypeptide of the present invention and the like”) to act on a mixture containing L-menthol and D-menthol.

In the method for producing L-menthol ester of the present invention, the polypeptide of the present invention and the like are preferably used in the form of an immobilized polypeptide in which the polypeptide is immobilized on a carrier.

The polypeptide of the present invention and the like can exhibit an excellent ester conversion rate of L-menthol in view of its transesterification activity value as well as improve the substrate specificity for L-menthol. Therefore, the polypeptide of the present invention and the like used in the method for producing L-menthol ester effectively exhibits a high ester conversion rate of L-menthol even when the transesterification activity value thereof is less than the transesterification activity value of the wild-type lipase of SEQ ID NO: 1. From such a viewpoint, the transesterification activity value of the polypeptide of the present invention and the like may be, for example, 0.3 to 0.8 times, preferably 0.45 to 0.7 times, and more preferably 0.55 to 0.6 times as the ratio with respect to the transesterification activity value of the same mass of the wild-type lipase of SEQ ID NO: 1 (the ratio of the transesterification activity value).

(Method for Deriving Ratio of Transesterification Activity Value)

A wild-type lipase of SEQ ID NO: 1 or a modified lipase of the present invention is reacted with phenylethyl alcohol (20 parts by weight) and vinyl acetate (80 parts by weight) as substrates at 30° C. for 20 minutes to perform a transesterification reaction. The obtained phenylethyl alcohol acetyl ester is quantified by HPLC analysis. When the amount of the phenylethyl alcohol acetyl ester obtained by the wild-type lipase (transesterification activity value of the wild-type lipase) is set to 1, the amount of the phenylethyl alcohol acetyl ester obtained by the modified lipase of the present invention (ester activity value by the modified lipase of the present invention) is regarded as the ratio of the transesterification activity value.

The polypeptide of the present invention and the like can be used, for example, in an amount of 0.01 to 200 mg, preferably 0.03 to 20 mg, and more preferably 0.05 to 1 mg, with respect to 1 g of L-menthol.

Examples of the acylating agent include carboxylic acids represented by general formula $R^2COOH$ and esters thereof, and examples of the esters include carboxylic acid alkyl esters represented by general formula $R^2COOR^3$, and carboxylic acid vinyl esters represented by general formula $R^2COOCH{=}CH_2$.

In the general formula, $R^2$ represents a linear or branched alkyl group having 1 to 20 carbon atoms, preferably 1 to 6 carbon atoms, a cycloalkyl group having 3 to 8 carbon atoms, an aryl group having 6 to 14 carbon atoms, an aralkyl group having 7 to 15 carbon atoms, an alkoxy group having 1 to 20 carbon atoms, or an alkylamino group having 1 to 20 carbon atoms, and $R^3$ represents a linear or branched alkyl group having 1 to 20 carbon atoms, preferably 1 to 6 carbon atoms. The alkyl group, the cycloalkyl group, the aryl group, the aralkyl group, the alkyl group of the alkoxy group, and the alkyl group of the alkylamino group may be unsubstituted or substituted, and examples of a substituent in the case of being substituted include a hydroxyl group, a formyl group, an alkoxy group having 1 to 6 carbon atoms, a carboxyl group, a mercapto group, a sulfo group, an amino group, an alkylamino group having 1 to 6 carbon atoms, a nitro group, and a halogen group. These acylating agents may be used singly or in combination of a plurality of kinds thereof.

In the method for producing L-menthol ester of the present invention, the polypeptide of the present invention and the like can be allowed to act on a mixture containing L-menthol and D-menthol together with an acylating agent. Examples of the acylating agent preferably include esters of carboxylic acids, more preferably include carboxylic acid vinyl esters, further preferably include vinyl acetate, vinyl propionate, vinyl butanoate, vinyl caproate, vinyl caprylate, vinyl caprate, vinyl laurate, vinyl myristate, vinyl palmitate, vinyl stearate, vinyl pivalate, vinyl octylate, vinyl benzoate, vinyl isovalerate, acetic anhydride, vinyl butyrate, vinyl chloroacetate, and propionic anhydride, and even more preferably include vinyl acetate.

The acylating agent can be used, for example, in an amount of 0.5 to 3 mol, preferably 0.8 to 2 mol, more preferably 1 to 1.5 mol, and further preferably 1.1 to 1.3 mol, with respect of 1 mol of L-menthol.

In the method for producing L-menthol ester of the present invention, a solvent used in the mixture containing L-menthol and D-menthol is a non-aqueous solvent. The non-aqueous solvent is an organic solvent which does not substantially contain water, and examples of such an organic solvent include hydrocarbon-based solvents such as pentane, hexane, heptane, and octane; ether-based solvents such as diethyl ether, methyl-t-butyl ether, dibutyl ether, and tetrahydrofuran; aromatic solvents such as toluene, xylene, and benzene; and halogen-based solvents such as dichloromethane and chloroform. Among these organic solvents, hydrocarbon-based solvents are preferably mentioned, and heptane is more preferably mentioned. These organic solvents may be used singly or in combination of a plurality of kinds thereof. The expression "does not substantially contain water" means that the case of containing a trace amount of water that does not affect the esterification reaction is allowed in addition to the case of not containing water at all, and a specific amount of the trace amount of water is, for example, an amount of a trace amount of water that can be mixed by moisture in a storage environment of a solvent or the like, specifically, 1000 ppm or less, preferably, 500 ppm or less.

The use amount of these solvents may be an amount that completely dissolves the mixture containing L-menthol and D-menthol, and is, for example, 0.3 to 3 ml, preferably 0.5 to 2 ml, and more preferably 0.8 to 1.5 ml, per 1 g of the total weight of L-menthol and D-menthol.

The specific operation in the method for producing L-menthol ester of the present invention is not particularly limited as long as a transesterification system in which a mixture containing L-menthol and D-menthol, an acylating agent, the polypeptide of the present invention and the like coexist can be constructed, but for example, L-menthol and D-menthol (DL-menthol (racemate)) are dissolved in the solvent, an acylating agent is added thereto and mixed, and the polypeptide of the present invention and the like can be further mixed. In the transesterification system, among L-menthol and D-menthol, L-menthol is specifically transesterified.

Since the polypeptide of the present invention is excellent in substrate specificity for L-menthol, in the method for producing L-menthol ester of the present invention, even when the transesterification rate of L-menthol is relatively high (that is, even when a large amount of D-menthol is present in the transesterification system), L-menthol ester having a high optical purity can be obtained. From this viewpoint, in the method for producing L-menthol ester of the present invention, the timing for terminating the reaction in the transesterification system can be set to a timing at which the transesterification rate of L-menthol is 80% or more, 85% or more, 90% or more, 93% or more, or 95% or more. The upper limit of the range of the transesterification rate of L-menthol is not particularly limited, and may be, for example, 99% or less, preferably 97% or less, or more preferably 96% or less, from the viewpoint of obtaining a high optical purity.

The obtained L-menthol ester can be purified by fractional extraction, fractional distillation, column chromatography, or the like.

L-menthol ester obtained in this way may be used, as L-menthol ester, for a perfume compound; an additive of food and drink, a cosmetic, a pharmaceutical, or a quasi-pharmaceutical product; an active ingredient of a cosmetic, a pharmaceutical, or a quasi-pharmaceutical product; an intermediate of an active ingredient of a cosmetic, a pharmaceutical, or a quasi-pharmaceutical product; or the like, and may be further used as a raw material for L-menthol. In the case of using L-menthol ester obtained from L-menthol ester of the present invention as a raw material for L-menthol, L-menthol can be produced by chemical hydrolysis with an acid or an alkali.

8-4. Method for Producing L-Menthol

A method for producing L-menthol of the present invention includes a step of hydrolyzing L-menthol ester by allowing the polypeptide of the present invention, the enzyme composition of the present invention, or the enzyme preparation of the present invention (the polypeptide of the present invention and the like) to act on a mixture containing L-menthol ester and D-menthol ester.

In the method for producing L-menthol of the present invention, the polypeptide of the present invention and the like are preferably used in the form of a free polypeptide.

The polypeptide of the present invention and the like can exhibit an excellent L-menthol conversion rate for its lipase activity value as well as improve the substrate specificity for L-menthol ester. Therefore, the polypeptide of the present invention and the like used in the method for producing L-menthol effectively exhibits a high L-menthol conversion rate even when the lipase activity value thereof is less than the lipase activity value of the wild-type lipase of SEQ ID NO: 1. From such a viewpoint, the lipase activity value of the polypeptide of the present invention and the like may be, for example, 0.1 to 0.95 times, preferably 0.2 to 0.9 times, more preferably 0.3 to 0.8 times, further preferably 0.4 to 0.7 times, and even more preferably 0.5 to 0.6 times as the ratio with respect to the lipase activity value of the same mass of the wild-type lipase of SEQ ID NO: 1 (the ratio of the lipase activity value).

(Method for Deriving Ratio of Lipase Activity Value)

The lipase activity value is measured by the following procedure using Lipase Kit S (DS Pharma Biomedical Co., Ltd.). An activity measuring solution is prepared by mixing 1 mL of the chromogenic solution attached to the kit, 20 μL of the esterase inhibitor solution attached to the kit, 1 mL of the buffer solution attached to the kit, 100 μL of the substrate solution attached to the kit, and 8 mL of water are mixed to prepare an activity measuring solution. To 100 μL of the activity measuring solution, 10 μL of an enzyme solution prepared by diluting the wild-type lipase of SEQ ID NO: 1 or the polypeptide of the present invention to an appropriate concentration with a 20 mM potassium phosphate buffer solution (pH 7.0) is added, and the absorbance at 412 nm after the reaction at 37° C. for 15 minutes is measured. As for a blank, a 20 mM potassium phosphate buffer solution (pH 7.0) is used instead of the enzyme solution. A value obtained by multiplying the absorbance difference between the wild-type lipase or the polypeptide of the present invention and the blank by a coefficient of 1.3 and a dilution factor is calculated as the lipase activity value (U/mL), and the ratio of the value obtained by the modified lipase of the present invention when the value obtained by the wild-type lipase is set to 1 is calculated.

The polypeptide of the present invention and the like can be used, for example, in an amount of 0.1 to 1000 mg preferably 1 to 100 mg, with respect to 1 g of L-menthol ester. The polypeptide of the present invention can be used, for example, in an amount of 500 to 50000 U and preferably 1000 to 30000 U as lipase activity, with respect to 1 g of L-menthol ester.

In the method for producing L-menthol of the present invention, a solvent used in the mixture containing L-menthol ester and D-menthol ester contains at least water. An organic solvent may be mixed in the solvent in addition to water, and examples of such an organic solvent include hydrocarbon-based solvents such as pentane, hexane, heptane, and octane; ether-based solvents such as diethyl ether, methyl-t-butyl ether, dibutyl ether, and tetrahydrofuran; aromatic solvents such as toluene, xylene, and benzene; halogen-based solvents such as dichloromethane and chloroform; alcohol-based solvents such as methanol, ethanol, propanol, and isopropanol; and ketone-based solvents such as acetone, methyl ethyl ketone, and methyl isobutyl ketone. These organic solvents may be used singly or in combination of a plurality of kinds thereof.

The reaction temperature is, for example, 10 to 50° C., preferably 20 to 45° C., more preferably 30 to 40° C., and further preferably 33 to 38° C.

The specific operation in the method for producing L-menthol of the present invention is not particularly limited as long as a hydrolysis system in which a mixture containing both L-menthol ester and D-menthol ester together with water, the polypeptide of the present invention and the like coexist can be constructed, but for example, L-menthol ester and D-menthol ester (DL-menthol ester (racemate)) are mixed in the solvent, and the polypeptide of the present invention and the like can be further mixed. In the hydrolysis system, among L-menthol ester and D-menthol ester, L-menthol ester is specifically hydrolyzed.

Since the polypeptide of the present invention is excellent in substrate specificity for L-menthol ester, in the method for producing L-menthol of the present invention, even when exchange rate for L-menthol is relatively high, L-menthol having a high optical purity can be obtained.

The obtained L-menthol can be purified by removing unreacted substances by fractional extraction, fractional distillation, column chromatography, or the like.

EXAMPLES

Hereinafter, the present invention will be described in more detail by means of Examples; however, the present invention is not limited to these Examples.

Test Example 1: Substrate Specificity-1 for L-Menthol Ester in Hydrolysis

[1-1. Case of Using Each of D-Menthyl Acetate and L-Menthyl Acetate as Substrate]

In this test example, each of D-menthyl acetate (purity: 98% or more, manufactured by Tokyo Chemical Industry Co., Ltd., in the form of oil, d=0.9250 to 0.9280) and L-menthyl acetate (purity: 98% or more, manufactured by Tokyo Chemical Industry Co., Ltd., in the form of oil, d=0.9250 to 0.9280) as a substrate was reacted with a *Burkholderia cepacia*-derived lipase (PS lipase) or various mutants thereof (free enzymes), and each reaction product thus obtained was analyzed by gas chromatography to examine the substrate specificity for L-menthol ester.

As mutants of the *Burkholderia cepacia*-derived lipase, those described in Table 1 were prepared. Specifically, an enzyme extract containing each mutant was prepared by the following method.

(Construction of Plasmid for *E. coli* Expression)

In constructing the *E. coli* expression system, genes in which each gene (LipA; Lipase LipA gene (*E. coli* codon optimization): SEQ ID NO: 4, LipX; Chaperone gene (LipX) wild type: SEQ ID NO: 5) of *B. cepacia* M12-33 was codon optimized for *E. coli* expression were totally synthesized.

A linker sequence (Nco I, Hind III) was added by PCR amplification (PrimeSTAR GXL DNA Polymerase (TaKaRa)), primer (forward primer: 5'-TTTTCCATGGCTCGTTCTATGCGTTCTCG-3': SEQ ID NO: 6, reverse primer: 5'-AAAAAAGCTTAAACACCCGCCAGTTTCAGACGG-3': SEQ ID NO: 7)) using the total synthesized structural gene (LipA; SEQ ID NO: 4) as a template, and then purification (NucleoSpin Gel and PCR Clean-up (MACHEREY-NAGEL)) was performed to obtain a gene fragment (BCL-LipA).

The gene fragment (BCL-LipA) and pETDuet-1 (Novagen) were treated with a restriction enzyme (Nco I (TaKaRa), Hind III (TaKaRa)), then ligated (DNA Ligation Kit <Mighty Mix> (TaKaRa)), and transformed into *E. coli* DH5a (TaKaRa) to obtain *E. coli* BCL-LipA. Plasmid extraction from *E. coli* BCL-LipA was performed using NucleoSpin Plasmid EasyPure (MACHEREY-NAGEL) after inoculating into LB Broth Base (invitrogen)+Amp: 100 μg/mL: 5 mL and shaking culture (37° C., 16 h, 140 rpm), thereby obtaining a plasmid (pETBCL-LipA).

The same operation was performed for Chaperone gene (LipX). That is, a linker sequence (Nde I, Xho I) was added by PCR amplification (primer (forward primer: 5'-TTTTCATATGACCGCACGTGAAGGTCGCGC-3': SEQ ID NO: 9, reverse primer: 5'-AAAACTCGAGTTACTGTGCAGAACCCGCACCG-3': SEQ ID NO: 10) using the total synthesized Chaperone gene (LipX; Chaperone gene LipX (*E. coli* codon optimization: SEQ ID NO: 8) as a template and then purification (NucleoSpin Gel and PCR Clean-up (MACHEREY-NAGEL)) was performed to obtain a gene fragment (BCL-LipX).

The gene fragment (BCL-LipX) and pETBCL-LipA were treated with a restriction enzyme (NdeI (TaKaRa), Xho I (TaKaRa)), then ligated, and transformed into *E. coli* DH5α to obtain *E. coli* BCL-LipAX. Plasmid extraction from *E. coli* BCL-LipAX was performed using NucleoSpin Plasmid EasyPure (MACHEREY-NAGEL) after inoculating into LB Broth Base+Amp: 100 μg/mL: 5 mL and shaking culture (37° C., 16 h, 140 rpm), thereby obtaining an *E. coli* expression plasmid (pETBCL-LipAX).

(Construction of *E. coli* Expression System)

The obtained *E. coli* expression plasmid (pETBCL-LipAX) was transformed into *E. coli* BL21 (DE3) (Nippongene) to obtain an *E. coli* expressing strain: *E. coli* BL21 (BCL-LipAX).

(Production of Random Mutant Strain)

Primers were designed to generate a saturated mutational library for the mutation sites.

A120X Primer:

```
(forward primer:
5'-NNKGATTTCGTTCAGGGCGTTCTGGC-3':
SEQ ID NO: 11),

reverse primer:
5'-GAATTCAGAACCGCGATGCGGAGTG-3':
SEQ ID NO: 12)
```

Mutation introduction into a mutation site was performed by PCR amplification (PrimeSTAR GXL DNA Polymerase (TaKaRa)) using Primer with a plasmid (pETBCL-LipAX) as a template. After the PCR amplification, a template plasmid treatment (37° C., 16 h) using Dpn I (TaKaRa) and a ligation reaction (16° C., o/n) using T4 polymerase (Toyobo) and Ligation High (Toyobo) were performed, and then transformation into *E. coli* BL21 (DE3) was performed, thereby obtaining a random mutant strain (*E. coli* BL21 (BCL-A120X)) into which a random mutation was introduced at a mutation site.

(Production of Mutational Library Using Teriffic Broth (Amp: 100 μg/mL))

In order to prepare a mutant strain library for a mutation site, the mutant strain selected above was inoculated into Teriffic Broth (invitrogen) (Amp: 100 μg/mL): 1 mL, and shake-cultured (33° C., 48 h) with a shake-culturing machine (Taitec). The induction of enzyme expression was performed by adding IPTG to the culture solution so that the final concentration reached 0.1 mM at the time point of culture: 24 h. After the culturing, bacterial cells were recovered by centrifugation (3,300 g×15 min, 4° C.), a lysis treatment (25° C., 1,000 rpm) using B-PER (ThermoFisher) and then centrifugation (3,300 g×15 min, 4° C.) were performed to recover the supernatant, and thus an enzyme extract containing a modified lipase was obtained.

In a reaction vessel (96-well plate), 200 μL of the obtained enzyme extract containing a modified lipase (used in a range of 10 to 200 U in terms of lipase activity; the solvent is water; the protein concentration is about 20 mg/mL) and 12 μL of the substrate were put and mixed, and hydrolysis was performed under conditions of 35° C., 1,000 rpm, and 72 hours using a plate shaker. In a reaction vessel (96-well plate), a wild-type lipase having a protein concentration of 20 mg/mL and 12 μL of the substrate were put and mixed, and hydrolysis was performed under conditions of 35° C., 1,000 rpm, and 72 hours using a plate shaker.

(Method for Measuring Ratio of Lipase Activity Value)

The lipase activity value was measured by the following procedure using Lipase Kit S (DS Pharma Biomedical Co., Ltd.). An activity measuring solution was prepared by mixing 1 mL of the chromogenic solution attached to the kit, 20 μL of the esterase inhibitor solution attached to the kit, 1 mL of the buffer solution attached to the kit, 100 μL of the substrate solution attached to the kit, and 8 mL of water were mixed to prepare an activity measuring solution. To 100 μL of the activity measuring solution, 10 μL of an enzyme solution prepared by diluting the wild-type lipase of SEQ ID NO: 1 or the polypeptide of the present invention to an appropriate concentration with a 20 mM potassium phosphate buffer solution (pH 7.0) was added, and the absorbance at 412 nm after the reaction at 37° C. for 15 minutes was measured. As for a blank, a 20 mM potassium phosphate buffer solution (pH 7.0) was used instead of the enzyme solution. A value obtained by multiplying the absorbance difference between the wild-type lipase or the polypeptide of the present invention and the blank by a coefficient of 1.3 and a dilution factor was calculated as the lipase activity value (U/mL), and the ratio of the value obtained by the modified lipase of the present invention when the value obtained by the wild-type lipase was set to 1 was calculated.

The reaction mixture solution was transferred to a 1.5 mL Eppendorf tube, 12 μL of a 6 M hydrochloric acid solution and 200 μL of heptane were added thereto and mixed by vortexing, then the mixture was centrifuged (15,000 rpm, 10 min, 25° C.), and 150 μL of a heptane layer (upper layer) was collected in a vial bottle for instrumental analysis to extract a reaction product. To the obtained heptane layer, 150 μL of heptane was further added and diluted to prepare 300 μL of an analysis sample.

By subjecting 300 μL of the analysis sample to gas chromatography under the following conditions, the amounts of the residual raw material and the reaction product were analyzed based on the chromatography peak area.

(Gas Chromatography Analysis Conditions)

Column: CP-Chiral-DEX CB (0.25 mm ID×25 m, J&W)

Injection amount: 1 μL

Inlet temperature: 200° C.

Injection method: Split 1:100

Carrier gas: He

Flow rate: 1.3 mL/min

Oven: 130° C., 8 minutes

Detector: FID, 300° C. ($H_2$: 40 mL/min, $O_2$: 400 mL/min)

The L-menthol conversion rate in the case of using L-menthyl acetate as a substrate was calculated based on the following formula. Results are shown in Table 1.

[Mathematical Formula 1]

$$L\text{-Menthol conversion rate}(\%) = \frac{(L\text{-Menthol production amount})}{(L\text{-Menthyl acetate residual amount} + L\text{-Menthol production amount})} \times 100$$

Also in the case of using D-menthyl acetate as a substrate, the D-menthol conversion rate (%) was calculated in the same manner as in the above formula, and L/D conversion rate ratio (substrate specificity for the L-form) was calculated based on the following formula. Results are shown in Table 1.

[Mathematical Formula 2]

$$L/D\ \text{conversion rate ratio}\ (\%) = \frac{L\text{-Menthol conversion rate}}{D\text{-Menthol conversion rate}}$$

TABLE 1

| | Amino acid substitution | L-Menthol conversion rate (%) | L/D conversion rate ratio (%) |
|---|---|---|---|
| Comparative Example 1 | (Wild-type) | 17.7 | 115 |
| Comparative Example 2 | A120C | 1.9 | 14 |
| Comparative Example 3 | A120D | 0.2 | 1 |
| Comparative Example 4 | A120B | 0.2 | 1 |
| Comparative Example 5 | A120F | 4.3 | 25 |
| Example 1 | A120G | 46.4 | 152 |
| Comparative Example 6 | A120H | 0.5 | 3 |
| Comparative Example 7 | A120I | 3.8 | 24 |
| Comparative Example 8 | A120K | 0.2 | 1 |
| Comparative Example 9 | A120L | 2.7 | 18 |
| Comparative Example 10 | A120M | 1.7 | 11 |
| Comparative Example 11 | A120N | 0.3 | 2 |
| Comparative Example 12 | A120P | 0.3 | 2 |
| Comparative Example 13 | A120Q | 0.2 | 2 |
| Comparative Example 14 | A120R | 0.2 | 2 |
| Comparative Example 15 | A120S | 11.1 | 87 |
| Comparative Example 16 | A120T | 4 | 31 |
| Comparative Example 17 | A120V | 3 | 18 |
| Comparative Example 18 | A120W | 1.6 | 8 |
| Comparative Example 19 | A120Y | 0.6 | 5 |

As apparent from Table 1, among mutants at the 120th position of the PS lipase (wild type; Comparative Example 1), only the A120G mutant (Example 1) was found to have especially high substrate specificity for the L-form than the wild type. According to the A120G mutant, it was found that the conversion rate of L-menthol is also excellent.

[1-2. Case of Using DL-Menthyl Acetate as Substrate]

Hydrolysis was performed in the same manner as in the above section 1-1, except that the wild-type lipase (Comparative Example 1) or the modified lipase of the present invention (Example 1) was used as an enzyme, and the substrate was changed to DL-menthyl acetate (purity: 98% or more, manufactured by Tokyo Chemical Industry Co., Ltd., in the form of oil, d=0.9250 to 0.9280).

The lipase activity values of the same mass of the wild-type lipase (Comparative Example 1) and the modified lipase of the present invention (Example 1) were measured, and the ratio thereof was derived. Results are shown in Table 2.

TABLE 2

| | PS lipase | Lipase activity ratio |
|---|---|---|
| Comparative Example 1 | Wild-type | 1 |
| Example 1 | A120G | 0.54 |

The optical purity of L-menthol in the case of using DL-menthyl acetate as a substrate was calculated based on the following formula. Results are shown in Table 3.

[Mathematical Formula 3]

$$\text{Optical purity}\ (\%\ ee) = \frac{[L\text{-Menthol amount}] - [D\text{-Menthol amount}]}{[DL\text{-Menthol amount}]} \times 100$$

TABLE 3

| | PS lipase | L-form conversion rate (%) | Optical purity (% e.e.) |
|---|---|---|---|
| Comparative Example 1 | Wild-type | 12.6 | 96.4 |
| Example 1 | A120G | 48.3 | 97.5 |

As apparent from Table 3, according to the modified lipase of the present invention (Example 1), although the L-form conversion rate was higher than that of the wild-type lipase (Comparative Example 1), improvement in optical purity was recognized. As shown in Table 2, in the modified lipase of the present invention (Example 1), although the lipase activity itself was significantly reduced as compared to the wild-type lipase (Comparative Example 1), improvement in L-form conversion rate as shown in Table 3 was recognized.

Test Example 2: Substrate Specificity for L-Menthol in Transesterification Reaction In this test example, DL-menthol (purity: 98% or more, manufactured by Tokyo Chemical Industry Co., Ltd., racemate, in the form of solid) as a substrate was reacted with a mutant (solid enzyme) obtained by converting A at the 120th position of a *Burkholderia cepacia*-derived lipase (PS lipase) to G, and the reaction product thus obtained was analyzed by gas chromatography to examine the substrate specificity for L-menthol in the transesterification reaction.

A modified lipase in which A at the 120th position of a *Burkholderia cepacia*-derived lipase (PS lipase) was converted to G was immobilized on a carrier (silica particle) according to a conventional method to obtain an immobilized enzyme (Example 2). A wild-type lipase was also immobilized in the same manner to obtain an immobilized enzyme (Comparative Example 20). The wild-type lipase or the modified lipase accounts for about 0.2 to 2 wt % of the obtained immobilized enzyme.

The ratio of the transesterification activity value of the same mass of the immobilized enzyme of the wild-type lipase (Comparative Example 20) and the immobilized enzyme of the modified lipase (Example 2) was measured by the following method. Results are shown in Table 4.

(Method for Measuring Transesterification Activity Value Ratio)

Each immobilized enzyme was reacted with phenylethyl alcohol (20 parts by weight) and vinyl acetate (80 parts by weight) as substrates at 30° C. for 20 minutes to perform a transesterification reaction. The obtained phenylethyl alcohol acetyl ester was quantified by HPLC analysis. When the amount of the phenylethyl alcohol acetyl ester obtained by the wild-type lipase (transesterification activity value of the wild-type lipase) was 1, the amount of the phenylethyl alcohol acetyl ester obtained by the modified lipase of the present invention (ester activity value by the modified lipase of the present invention) was regarded as the ratio of the transesterification activity value.

TABLE 4

| | PS lipase | Transesterification activity value ratio |
|---|---|---|
| Comparative Example 20 | Wild-type (immobilized) | 1 |
| Example 2 | A120G (immobilized) | 0.58 |

In 52.5 ml of heptane, 50 g of DL-menthol was dissolved, and 15.4 g of vinyl acetate as an acylating agent was further added and mixed (before the enzyme reaction). The reaction was started by adding 2 g of the immobilized enzyme and stirring the resultant mixture at 25° C. After the reaction for 18 hours, the immobilized enzyme was removed by filtration with filter paper to obtain a reaction filtrate. To 100 µl of the reaction filtrate, 20 µl of an internal standard solution was added, and 25 µl of the resultant mixture was diluted with 1 ml of heptane to prepare an analysis sample.

By subjecting the analysis sample to gas chromatography under the following conditions, the reaction product was analyzed.

(Gas Chromatography Analysis Conditions)

Column: CP-Chiral-DEX CB (0.25 mm ID×25 m, J&W)

Injection amount: 1 µL

Inlet temperature: 25° C.

Injection method: Split 1:100

Carrier gas:

Flow rate: 1.3 mL/min

Oven: 110° C., 25 minutes

Detector: FID, 300° C.

The L-menthyl acetate conversion rate (L-form conversion rate) in the reaction product was calculated based on the following formula. Results are shown in Table 5.

[Mathematical Formula 4]

$$L\text{-Menthyl acetate conversion rate (\%)} = \frac{L\text{-Menthol amount after reaction}}{L\text{-Menthol amount before reaction}} \times 100$$

The optical purity of the reaction product was calculated based on the following formula. Results are shown in Table 3.

[Mathematical Formula 5]

$$\text{Optical purity (\% } ee) = \frac{[L\text{-Menthyl acetate amount}] - [D\text{-Menthyl acetate amount}]}{DL\text{-Menthyl acetate amount}} \times 100$$

TABLE 5

| | PS lipase | L-form conversion rate (%) | Optical purity ee (%) |
|---|---|---|---|
| Comparative Example 20 | Wild-type (immobilized) | 95.6 | 98.3 |
| Example 2 | A120G (immobilized) | 95 | 99.5 |

As apparent from Table 5, according to the modified lipase of the present invention (Example 2), although the L-form conversion rate was equivalent to that of the wild-type lipase (Comparative Example 20), improvement in optical purity was recognized. As shown in Table 4, in the modified lipase of the present invention (Example 2), although the ester activity value itself was significantly reduced as compared to the wild-type lipase (Comparative Example 20)), a decrease in L-form conversion rate as shown in Table 5 was not almost recognized.

Test Example 3: Substrate Specificity-2 for L-Menthol Ester in Hydrolysis

The same operation as in Test Example 1 was performed, except that the polypeptides shown in Table 6 were prepared as mutants of the *Burkholderia cepacia*-derived lipase using appropriately designed primers, to examine the substrate specificity of the mutants for L-menthol ester in hydrolysis. Results are shown in Table 6.

TABLE 6

| | Amino acid substitution | L-Menthol conversion rate (%) | L/D conversion rate ratio (%) |
|---|---|---|---|
| Comparative Example 21 | (Wild-type) | 14 | 84 |
| Example 3 | Q88A | 50 | 351 |
| Example 4 | Q88G | 54 | 307 |
| Example 5 | Q88D | 40 | 269 |
| Example 6 | Q88M | 45 | 206 |
| Example 7 | Q88L | 15 | 107 |
| Comparative Example 22 | Q88F | 10 | 64 |
| Comparative Example 23 | Q88S | 6 | 48 |
| Comparative Example 24 | Q88Y | 7 | 42 |
| Comparative Example 25 | Q88H | 4 | 32 |
| Comparative Example 26 | Q88E | 3 | 24 |
| Comparative Example 27 | Q88V | 3 | 22 |
| Comparative Example 28 | Q88N | 3 | 21 |
| Comparative Example 29 | Q88I | 2 | 18 |
| Comparative Example 30 | Q88K | 1 | 12 |
| Comparative Example 31 | Q88W | 2 | 12 |
| Comparative Example 32 | Q88T | 1 | 10 |
| Comparative Example 33 | Q88P | 1 | 9 |
| Comparative Example 34 | Q88C | 1 | 9 |
| Comparative Example 35 | Q88R | 1 | 6 |

As apparent from Table 6, among mutants at the 88th position of the PS lipase (wild type; Comparative Example 21), only the Q88A mutant (Example 3), the Q88G mutant (Example 4), the Q88D mutant (Example 5), the Q88M mutant (Example 6), and the Q88L mutant (Example 7) were found to have higher substrate specificity for the L-form than the wild type. It was found that the Q88A mutant, the Q88G mutant, the Q88D mutant, the Q88M mutant, and the Q88L mutant were also especially excellent in the conversion rate of L-menthol.

SEQUENCE LISTING FREE TEXT

SEQ ID NO: 3 is a DNA encoding the A120G mutant of the *Burkholderia cepacia*-derived lipase.

SEQ ID NO: 6 is a forward primer of LipA.

SEQ ID NO: 7 is a reverse primer of LipA.

SEQ ID NO: 9 is a forward primer of LipX.

SEQ ID NO: 10 is a reverse primer of LipX.

SEQ ID NO: 11 is a forward primer of A120X.

SEQ ID NO: 12 is a reverse primer of A120X.

SEQ ID NO: 13 is a DNA encoding the Q88A mutant of the *Burkholderia cepacia*-derived lipase.

SEQ ID NO: 14 is a DNA encoding the Q88G mutant of the *Burkholderia cepacia*-derived lipase.

SEQ ID NO: 15 is a DNA encoding the Q88D mutant of the *Burkholderia cepacia*-derived lipase.

SEQ ID NO: 16 is a DNA encoding the Q88M mutant of the *Burkholderia cepacia*-derived lipase.

SEQ ID NO: 17 is a DNA encoding the Q88L mutant of the *Burkholderia cepacia*-derived lipase.

---

The invention claimed is:

1. A polypeptide of any one of the following (1) to (3):

(1) a polypeptide comprising the amino acid sequence of SEQ ID NO: 1 in which the amino acid residue at the 120th position is substituted with a glycine residue;

(2) a polypeptide comprising an amino acid sequence in which an amino acid residue at the 120th position is substituted with a glycine residue in an amino acid sequence shown in SEQ ID NO: 1, and 1-20 amino acid residues other than the amino acid residue introduced by the substitution are substituted, added, inserted, or deleted; and (3) a polypeptide comprising an amino acid sequence in which an amino acid residue at the 120th position is substituted with a glycine residue in an amino acid sequence shown in SEQ ID NO: 1, having 90% or more sequence identity to an amino acid sequence shown in SEQ ID NO: 1 except for the amino acid residue introduced by the substitution.

2. A polypeptide of any one of the following (A) to (C):

(A) a polypeptide comprising the amino acid sequence of SEQ ID NO: 1 in which the amino acid residue at the 88th position is substituted with an alanine residue, a glycine residue, an aspartic acid residue, a methionine residue, or a leucine residue;

(B) a polypeptide comprising an amino acid sequence in which an amino acid residue at the 88th position is substituted with an alanine residue, a glycine residue, an aspartic acid residue, a methionine residue, or a leucine residue in an amino acid sequence shown in SEQ ID NO: 1, and 1-20 amino acid residues other than the amino acid residue introduced by the substitution are substituted, added, inserted, or deleted; and (C) a polypeptide comprising an amino acid sequence in which an amino acid residue at the 88th position is substituted with an alanine residue, a glycine residue, an aspartic acid residue, a methionine residue, or a leucine residue in an amino acid sequence shown in SEQ ID NO: 1, having 90% or more sequence identity to an amino acid sequence shown in SEQ ID NO: 1 except for the amino acid residue introduced by the substitution.

3. A DNA encoding the polypeptide according to claim 1.

4. A recombinant vector comprising the DNA according to claim 3.

5. A transformant obtained by transforming a host with the recombinant vector according to claim 4.

6. A method for producing the polypeptide according to claim 1, the method comprising a step of culturing a transformant that expresses the polypeptide according to claim 1.

7. An enzyme composition comprising the polypeptide according to claim 1.

8. A method for producing L-menthol ester, the method comprising a step of esterifying L-menthol by allowing the polypeptide according to claim 1 to act on a mixture containing L-menthol and D-menthol.

9. A method for producing L-menthol, the method comprising a step of hydrolyzing L-menthol ester by allowing the polypeptide according to claim 1 to act on a mixture containing L-menthol ester and D-menthol ester.

10. A DNA encoding the polypeptide according to claim 2.

11. A recombinant vector comprising the DNA according to claim 10.

12. A transformant obtained by transforming a host with the recombinant vector according to claim 11.

13. A method for producing the polypeptide according to claim 2, the method comprising a step of culturing a transformant that expresses the polypeptide according to claim 2.

14. An enzyme composition comprising the polypeptide according to claim 2.

15. A method for producing L-menthol ester, the method comprising a step of esterifying L-menthol by allowing the polypeptide according to claim 2 to act on a mixture containing L-menthol and D-menthol.

16. A method for producing L-menthol ester, the method comprising a step of esterifying L-menthol by allowing the enzyme composition according to claim 7 to act on a mixture containing L-menthol and D-menthol.

17. A method for producing L-menthol, the method comprising a step of hydrolyzing L-menthol ester by allowing the polypeptide according to claim 2 to act on a mixture containing L-menthol ester and D-menthol ester.

18. A method for producing L-menthol, the method comprising a step of hydrolyzing L-menthol ester by allowing the enzyme preparation according to claim 14 to act on a mixture containing L-menthol ester and D-menthol ester.

* * * * *

SEQUENCE LISTING

```
<160> NUMBER OF SEQ ID NOS: 17

<210> SEQ ID NO 1
<211> LENGTH: 320
<212> TYPE: PRT
<213> ORGANISM: Burkholderia cepacia

<400> SEQUENCE: 1

Ala Asp Asn Tyr Ala Ala Thr Arg Tyr Pro Ile Ile Leu Val His Gly
1               5                   10                  15

Leu Thr Gly Thr Asp Lys Tyr Ala Gly Val Leu Glu Tyr Trp Tyr Gly
            20                  25                  30

Ile Gln Glu Asp Leu Gln Gln Arg Gly Ala Thr Val Tyr Val Ala Asn
        35                  40                  45

Leu Ser Gly Phe Gln Ser Asp Asp Gly Pro Asn Gly Arg Gly Glu Gln
    50                  55                  60

Leu Leu Ala Tyr Val Lys Thr Val Leu Ala Ala Thr Gly Ala Thr Lys
65                  70                  75                  80

Val Asn Leu Val Gly His Ser Gln Gly Gly Leu Thr Ser Arg Tyr Val
                85                  90                  95

Ala Ala Val Ala Pro Asp Leu Val Ala Ser Val Thr Thr Ile Gly Thr
            100                 105                 110

Pro His Arg Gly Ser Glu Phe Ala Asp Phe Val Gln Gly Val Leu Ala
        115                 120                 125

Tyr Asp Pro Thr Gly Leu Ser Ser Thr Val Ile Ala Ala Phe Val Asn
    130                 135                 140

Val Phe Gly Ile Leu Thr Ser Ser Ser Asn Asn Thr Asn Gln Asp Ala
145                 150                 155                 160

Leu Ala Ala Leu Lys Thr Leu Thr Thr Ala Gln Ala Ala Thr Tyr Asn
                165                 170                 175

Gln Asn Tyr Pro Ser Ala Gly Leu Gly Ala Pro Gly Ser Cys Gln Thr
            180                 185                 190

Gly Ala Pro Thr Glu Thr Val Gly Gly Asn Thr His Leu Leu Tyr Ser
        195                 200                 205

Trp Ala Gly Thr Ala Ile Gln Pro Thr Ile Ser Val Phe Gly Val Thr
    210                 215                 220

Gly Ala Thr Asp Thr Ser Thr Ile Pro Leu Val Asp Pro Ala Asn Ala
225                 230                 235                 240

Leu Asp Pro Ser Thr Leu Ala Leu Phe Gly Thr Gly Thr Val Met Val
                245                 250                 255

Asn Arg Gly Ser Gly Gln Asn Asp Gly Val Val Ser Lys Cys Ser Ala
            260                 265                 270

Leu Tyr Gly Gln Val Leu Ser Thr Ser Tyr Lys Trp Asn His Leu Asp
        275                 280                 285

Glu Ile Asn Gln Leu Leu Gly Val Arg Gly Ala Asn Ala Glu Asp Pro
    290                 295                 300

Val Ala Val Ile Arg Thr His Ala Asn Arg Leu Lys Leu Ala Gly Val
```

-continued 305 310 315 320

<210> SEQ ID NO 2
<211> LENGTH: 1095
<212> TYPE: DNA
<213> ORGANISM: Burkholderia cepacia

<400> SEQUENCE: 2

```
atggccagat cgatgcgttc cagggtggtg gcaggggcag tggcatgcgc gatgagcgtc     60

gcgccgttcg cggggatgac cgcggcgatg acgctcgcga cgacgcgcgc ggcaatggcg    120

gcgagcgcgc ccgccgacaa ctacgcggcg acgcgttatc cgatcattct cgtgcacggg    180

ctcacgggca ccgacaaata cgcaggtgtg ctcgagtact ggtacgggat ccaggaggac    240

ctgcagcagc gtggcgcgac cgtctatgtc gctaacctgt cgggcttcca gagcgacgac    300

ggcccgaacg ggcgcggcga acagttgctg gcctacgtga agacggtgct cgccgcgacg    360

ggggcgacca aggtcaacct cgtcggccac agccagggcg ggctgacgtc gcgctatgtc    420

gcggccgtcg cgcccgatct ggtcgcgtcg gtgacgacga tcggcacgcc gcatcgcggc    480

tccgagttcg ccgacttcgt gcagggcgtg ctcgcgtacg atccgaccgg gctgtcgtcg    540

acggtgatcg ccgcgttcgt caatgtgttc ggaatcctca cgagcagcag caacaacacg    600

aaccaggacg cgctcgcggc gctgaagacg ctgacgaccg cgcaggccgc cacgtacaac    660

cagaactacc ctagcgcggg cctcggcgcg ccgggcagtt gccagaccgg cgcgccgacg    720

gaaaccgtcg gcggcaacac gcatctgctg tattcgtggg ccggcacggc gatccagccg    780

acgatctccg tgttcggcgt cacgggtgcg acggatacga gcaccattcc gctcgtcgat    840

ccggcgaacg cgctcgaccc gtcgacgctc gcgctgttcg gcaccggcac ggtgatggtc    900

aaccgcggtt cgggccagaa cgacggggtc gtgtcgaagt gcagcgcgct gtacggccag    960

gtgctgagca cgagctacaa gtggaaccat ctcgacgaga tcaaccagtt gctcggcgtg   1020

cgcggcgcga atgcggaaga tccggtcgcg gtgatccgca cgcatgcgaa ccggctgaag   1080

ctcgcgggcg tgtga                                                    1095
```

<210> SEQ ID NO 3
<211> LENGTH: 1095
<212> TYPE: DNA
<213> ORGANISM: Artificial Sequence
<220> FEATURE:
<223> OTHER INFORMATION: DNA coding a mutant A120G of lipase from Burkholderia cepacia

<400> SEQUENCE: 3

```
atggccagat cgatgcgttc cagggtggtg gcaggggcag tggcatgcgc gatgagcgtc     60

gcgccgttcg cggggatgac cgcggcgatg acgctcgcga cgacgcgcgc ggcaatggcg    120

gcgagcgcgc ccgccgacaa ctacgcggcg acgcgttatc cgatcattct cgtgcacggg    180

ctcacgggca ccgacaaata cgcaggtgtg ctcgagtact ggtacgggat ccaggaggac    240

ctgcagcagc gtggcgcgac cgtctatgtc gctaacctgt cgggcttcca gagcgacgac    300

ggcccgaacg ggcgcggcga acagttgctg gcctacgtga agacggtgct cgccgcgacg    360

ggggcgacca aggtcaacct cgtcggccac agccagggcg ggctgacgtc gcgctatgtc    420

gcggccgtcg cgcccgatct ggtcgcgtcg gtgacgacga tcggcacgcc gcatcgcggc    480

tccgagttcg gcgacttcgt gcagggcgtg ctcgcgtacg atccgaccgg gctgtcgtcg    540

acggtgatcg ccgcgttcgt caatgtgttc ggaatcctca cgagcagcag caacaacacg    600
```

-continued

```
aaccaggacg cgctcgcggc gctgaagacg ctgacgaccg cgcaggccgc cacgtacaac    660

cagaactacc ctagcgcggg cctcggcgcg ccgggcagtt gccagaccgg cgcgccgacg    720

gaaaccgtcg gcggcaacac gcatctgctg tattcgtggg ccggcacggc gatccagccg    780

acgatctccg tgttcggcgt cacgggtgcg acggatacga gcaccattcc gctcgtcgat    840

ccggcgaacg cgctcgaccc gtcgacgctc gcgctgttcg gcaccggcac ggtgatggtc    900

aaccgcggtt cgggccagaa cgacggggtc gtgtcgaagt gcagcgcgct gtacggccag    960

gtgctgagca cgagctacaa gtggaaccat ctcgacgaga tcaaccagtt gctcggcgtg   1020

cgcggcgcga atgcggaaga tccggtcgcg gtgatccgca cgcatgcgaa ccggctgaag   1080

ctcgcgggcg tgtga                                                    1095
```

<210> SEQ ID NO 4
<211> LENGTH: 1095
<212> TYPE: DNA
<213> ORGANISM: Burkholderia cepacia

<400> SEQUENCE: 4

```
atggctcgtt ctatgcgttc tcgtgttgtg gcaggtgctg tggcatgcgc aatgtctgtg     60

gcgccgtttg caggcatgac cgcagcgatg accctggcga ccacccgtgc ggcgatggct    120

gcgtctgcac cggctgacaa ctacgcagct actcgttacc cgatcatcct ggtgcatggt    180

ctgactggca ccgataagta tgctggtgtt ctggagtact ggtacggtat tcaggaagac    240

ctgcagcagc gtggcgcgac tgtttacgtt gcgaacctgt ctggtttcca gtccgacgac    300

ggcccgaacg gtcgcggcga acagctgctg gcgtatgtga aaactgtgct ggcggctacc    360

ggcgcaacca aagttaacct ggttggccac tcccagggtg gcctgacttc tcgctacgtg    420

gcagcggtgg ctccggacct ggtggcgagc gttactacca ttggcactcc gcatcgcggt    480

tctgaattcg cggatttcgt tcagggcgtt ctggcgtatg acccgactgg cctgtcttct    540

accgtgatcg cggcatttgt taacgttttt ggtatcctga cctcttccag caacaacact    600

aaccaggacg ctctggctgc actgaaaacc ctgaccaccg cgcaggctgc tacctacaac    660

cagaactatc cgtctgcggg tctgggcgct ccgggttctt gccagaccgg tgcgccgacc    720

gagactgtgg gtggcaacac tcacctgctg tactcttggg cgggtactgc gatccagccg    780

accatctctg ttttcggtgt tactggtgcg actgatacct ctactatccc gctggtggat    840

ccggcaaacg cactggaccc gtccactctg gcgctgtttg gtaccggcac cgttatggtg    900

aaccgtggta gcggtcagaa cgatggtgtg gtgtctaagt gctctgcgct gtacggccag    960

gttctgtcta cctcttacaa atggaaccac ctggacgaga tcaaccagct gctgggtgtt   1020

cgtggtgcta acgcggaaga tccggtggcg gtgattcgca ctcacgcaaa ccgtctgaaa   1080

ctggcgggtg tttaa                                                    1095
```

<210> SEQ ID NO 5
<211> LENGTH: 1034
<212> TYPE: DNA
<213> ORGANISM: Burkholderia cepacia

<400> SEQUENCE: 5

```
atgacggcac gtgaagggcg cgcgccgctg gcgcggcgcg ctgtggtcta cggttcgtgg     60

ggctggcggc gatcgccggc gtcgcgatgt ggagcggtgc gggatggcat cgcgggacgg    120

gcacggccgg cgagttgccg gacgcggcag cggcaggcgg ggcggctgcc gcaccgccgc    180

aggccgctct gccggcgagc acgggcctgc cgtcgtcgct ggccggctcc agtgcgccgc    240
```

-continued ggctgccgct cgatgccggc ggccatcttg cgaagtcgcg cgcggtgcgc gatttcttcg 300
actactgcct gaccgcgcag agtgacctga gcgcggccgc gctcgatgcg ttcgtcgtac 360
gccagatcgc cgcgcagctc gacggcacgg tcgcgcaggc cgaggcgctc gacgtctggc 420
accggtaccg cgcgtatctc gacgcgctcg cgaagttgcg cgatgccggc gcggtcgaca 480
agtccgacct gggtgcgctg cagctcgcgc tcgaccagcg cgcgtcgatc gcgtaccgca 540
cgctcggcga ctggagccag ccgtttttcg gcgcggagca gtggcggcag cgctacgatc 600
tcgcgcgact gaagatcgcg caggatcgta cgctgacgga tgcgcagaag gccgagcggc 660
tcgcggcgct tgagcagcag atgccagccg acgaacgcgc ggcgcagcag cgggtcgacc 720
agcagcgggc cgcgatcgac cggatcgcgc aactgcagaa gagcggcgcg acgcccgatg 780
cgatgcgcgc gcaactgacg cagacgctcg gcccggaagc cgccgcgcgc gtcgcgcaga 840
tgcagcagga cgacgcatcg tggcagagcc gctacgcgga ctatgcgacg cagcgtgcgc 900
agatcgagtc ggccggcctg tcgccgcagg atcgcgacgc ccagatcgcc gcattgcggc 960
agcgcacgtt cacgaaaccc ggcgaagcgg tgcgggcggc atcgctcgat cgcggcgcgg 1020
gcagcgcgca gtga 1034

<210> SEQ ID NO 6
<211> LENGTH: 29
<212> TYPE: DNA
<213> ORGANISM: Artificial Sequence
<220> FEATURE:
<223> OTHER INFORMATION: forward primer for LipA

<400> SEQUENCE: 6
ttttccatgg ctcgttctat gcgttctcg 29

<210> SEQ ID NO 7
<211> LENGTH: 33
<212> TYPE: DNA
<213> ORGANISM: Artificial Sequence
<220> FEATURE:
<223> OTHER INFORMATION: reverse primer for LipA

<400> SEQUENCE: 7
aaaaaagctt aaacacccgc cagtttcaga cgg 33

<210> SEQ ID NO 8
<211> LENGTH: 1035
<212> TYPE: DNA
<213> ORGANISM: Burkholderia cepacia

<400> SEQUENCE: 8
atgaccgcac gtgaaggtcg cgctccgctg gctcgtcgcg cagtggttta cggtgttgtt 60
ggtctggctg ctatcgcagg tgttgcgatg tggtccggtg ctggttggca tcgtggtacc 120
ggcactgcgg gcgaactgcc ggatgcagcg gctgcaggtg gtgctgcggc agctccgccg 180
caggcggctc tgccggcgtc tactggtctg ccgagcagcc tggcgggctc ttctgctccg 240
cgcctgccgc tggacgcggg tggtcacctg gctaaaagcc gtgctgttcg cgacttcttc 300
gactactgcc tgaccgcgca gagcgacctg agcgcagcag ctctggacgc ttttgttgtt 360
cgtcagattg cggctcagct ggatggcact gttgcgcagg ctgaagcact ggacgtgtgg 420
caccgttacc gtgcttacct ggatgcactg gcaaaactgc gtgatgcggg tgcagtggac 480
aaatctgatc tgggcgcact gcagctggcg ctggatcagc gtgcgtctat cgcgtaccgt 540

-continued

```
accctgggtg attggtctca gccgttcttc ggtgcggaac agtggcgtca gcgttacgac    600

ctggcgcgtc tgaaaatcgc gcaggatcgt accctgaccg acgcgcagaa agcggaacgt    660

ctggcggcac tggaacagca gatgccggct gatgagcgtg cagctcagca gcgtgtggac    720

cagcagcgcg cagctatcga tcgtatcgct cagctgcaga aatctggtgc gaccccggac    780

gcgatgcgtg cacagctgac tcagaccctg ggtccggagg cggcagctcg cgttgcacag    840

atgcagcagg acgatgcttc ctggcagtct cgctacgcgg actacgcgac ccagcgtgcg    900

cagattgaga gcgcgggtct gtctccgcag gaccgtgacg ctcagattgc tgcgctgcgt    960

cagcgtacct tcaccaaacc gggtgaagcg gttcgtgcgg cgtctctgga tcgcggtgcg   1020

ggttctgcac agtaa                                                    1035


<210> SEQ ID NO 9
<211> LENGTH: 30
<212> TYPE: DNA
<213> ORGANISM: Artificial Sequence
<220> FEATURE:
<223> OTHER INFORMATION: forward primer for LipX

<400> SEQUENCE: 9

ttttcatatg accgcacgtg aaggtcgcgc                                      30


<210> SEQ ID NO 10
<211> LENGTH: 32
<212> TYPE: DNA
<213> ORGANISM: Artificial Sequence
<220> FEATURE:
<223> OTHER INFORMATION: reverse primer for LipX

<400> SEQUENCE: 10

aaaactcgag ttactgtgca gaacccgcac cg                                   32


<210> SEQ ID NO 11
<211> LENGTH: 26
<212> TYPE: DNA
<213> ORGANISM: Artificial Sequence
<220> FEATURE:
<223> OTHER INFORMATION: forward primer for A120X
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(3)
<223> OTHER INFORMATION: k is g or t

<400> SEQUENCE: 11

nnkgatttcg ttcagggcgt tctggc                                          26


<210> SEQ ID NO 12
<211> LENGTH: 25
<212> TYPE: DNA
<213> ORGANISM: Artificial Sequence
<220> FEATURE:
<223> OTHER INFORMATION: reverse primer for A120X

<400> SEQUENCE: 12

gaattcagaa ccgcgatgcg gagtg                                           25


<210> SEQ ID NO 13
<211> LENGTH: 1095
<212> TYPE: DNA
<213> ORGANISM: Artificial Sequence
```

-continued

<220> FEATURE:
<223> OTHER INFORMATION: DNA coding a mutant Q88A of lipase from
Burkholderia cepacia

<400> SEQUENCE: 13

```
atggccagat cgatgcgttc cagggtggtg gcaggggcag tggcatgcgc gatgagcgtc     60

gcgccgttcg cggggatgac cgcggcgatg acgctcgcga cgacgcgcgc ggcaatggcg    120

gcgagcgcgc ccgccgacaa ctacgcggcg acgcgttatc cgatcattct cgtgcacggg    180

ctcacgggca ccgacaaata cgcaggtgtg ctcgagtact ggtacgggat ccaggaggac    240

ctgcagcagc gtggcgcgac cgtctatgtc gctaacctgt cgggcttcca gagcgacgac    300

ggcccgaacg ggcgcggcga acagttgctg gcctacgtga agacggtgct cgccgcgacg    360

ggggcgacca aggtcaacct cgtcggccac agcgcgggcg ggctgacgtc gcgctatgtc    420

gcggccgtcg cgcccgatct ggtcgcgtcg gtgacgacga tcggcacgcc gcatcgcggc    480

tccgagttcg ccgacttcgt gcagggcgtg ctcgcgtacg atccgaccgg gctgtcgtcg    540

acggtgatcg ccgcgttcgt caatgtgttc ggaatcctca cgagcagcag caacaacacg    600

aaccaggacg cgctcgcggc gctgaagacg ctgacgaccg cgcaggccgc cacgtacaac    660

cagaactacc ctagcgcggg cctcggcgcg ccgggcagtt gccagaccgg cgcgccgacg    720

gaaaccgtcg gcggcaacac gcatctgctg tattcgtggg ccggcacggc gatccagccg    780

acgatctccg tgttcggcgt cacgggtgcg acggatacga gcaccattcc gctcgtcgat    840

ccggcgaacg cgctcgaccc gtcgacgctc gcgctgttcg gcaccggcac ggtgatggtc    900

aaccgcggtt cgggccagaa cgacggggtc gtgtcgaagt gcagcgcgct gtacggccag    960

gtgctgagca cgagctacaa gtggaaccat ctcgacgaga tcaaccagtt gctcggcgtg   1020

cgcggcgcga atgcggaaga tccggtcgcg gtgatccgca cgcatgcgaa ccggctgaag   1080

ctcgcgggcg tgtga                                                    1095
```

<210> SEQ ID NO 14
<211> LENGTH: 1095
<212> TYPE: DNA
<213> ORGANISM: Artificial Sequence
<220> FEATURE:
<223> OTHER INFORMATION: DNA coding a mutant Q88G of lipase from
Burkholderia cepacia

<400> SEQUENCE: 14

```
atggccagat cgatgcgttc cagggtggtg gcaggggcag tggcatgcgc gatgagcgtc     60

gcgccgttcg cggggatgac cgcggcgatg acgctcgcga cgacgcgcgc ggcaatggcg    120

gcgagcgcgc ccgccgacaa ctacgcggcg acgcgttatc cgatcattct cgtgcacggg    180

ctcacgggca ccgacaaata cgcaggtgtg ctcgagtact ggtacgggat ccaggaggac    240

ctgcagcagc gtggcgcgac cgtctatgtc gctaacctgt cgggcttcca gagcgacgac    300

ggcccgaacg ggcgcggcga acagttgctg gcctacgtga agacggtgct cgccgcgacg    360

ggggcgacca aggtcaacct cgtcggccac agcgggggcg ggctgacgtc gcgctatgtc    420

gcggccgtcg cgcccgatct ggtcgcgtcg gtgacgacga tcggcacgcc gcatcgcggc    480

tccgagttcg ccgacttcgt gcagggcgtg ctcgcgtacg atccgaccgg gctgtcgtcg    540

acggtgatcg ccgcgttcgt caatgtgttc ggaatcctca cgagcagcag caacaacacg    600

aaccaggacg cgctcgcggc gctgaagacg ctgacgaccg cgcaggccgc cacgtacaac    660

cagaactacc ctagcgcggg cctcggcgcg ccgggcagtt gccagaccgg cgcgccgacg    720
```

-continued

```
gaaaccgtcg gcggcaacac gcatctgctg tattcgtggg ccggcacggc gatccagccg    780

acgatctccg tgttcggcgt cacgggtgcg acggatacga gcaccattcc gctcgtcgat    840

ccggcgaacg cgctcgaccc gtcgacgctc gcgctgttcg gcaccggcac ggtgatggtc    900

aaccgcggtt cgggccagaa cgacggggtc gtgtcgaagt gcagcgcgct gtacggccag    960

gtgctgagca cgagctacaa gtggaaccat ctcgacgaga tcaaccagtt gctcggcgtg   1020

cgcggcgcga atgcggaaga tccggtcgcg gtgatccgca cgcatgcgaa ccggctgaag   1080

ctcgcgggcg tgtga                                                     1095
```

<210> SEQ ID NO 15
<211> LENGTH: 1095
<212> TYPE: DNA
<213> ORGANISM: Artificial Sequence
<220> FEATURE:
<223> OTHER INFORMATION: DNA coding a mutant Q88D of lipase from
      Burkholderia cepacia

<400> SEQUENCE: 15

```
atggccagat cgatgcgttc cagggtggtg gcaggggcag tggcatgcgc gatgagcgtc     60

gcgccgttcg cggggatgac cgcggcgatg acgctcgcga cgacgcgcgc ggcaatggcg    120

gcgagcgcgc ccgccgacaa ctacgcggcg acgcgttatc cgatcattct cgtgcacggg    180

ctcacgggca ccgacaaata cgcaggtgtg ctcgagtact ggtacgggat ccaggaggac    240

ctgcagcagc gtggcgcgac cgtctatgtc gctaacctgt cgggcttcca gagcgacgac    300

ggcccgaacg ggcgcggcga acagttgctg gcctacgtga agacggtgct cgccgcgacg    360

ggggcgacca aggtcaacct cgtcggccac agcgacggcg ggctgacgtc gcgctatgtc    420

gcggccgtcg cgcccgatct ggtcgcgtcg gtgacgacga tcggcacgcc gcatcgcggc    480

tccgagttcg ccgacttcgt gcagggcgtg ctcgcgtacg atccgaccgg gctgtcgtcg    540

acggtgatcg ccgcgttcgt caatgtgttc ggaatcctca cgagcagcag caacaacacg    600

aaccaggacg cgctcgcggc gctgaagacg ctgacgaccg cgcaggccgc cacgtacaac    660

cagaactacc ctagcgcggg cctcggcgcg ccgggcagtt gccagaccgg cgcgccgacg    720

gaaaccgtcg gcggcaacac gcatctgctg tattcgtggg ccggcacggc gatccagccg    780

acgatctccg tgttcggcgt cacgggtgcg acggatacga gcaccattcc gctcgtcgat    840

ccggcgaacg cgctcgaccc gtcgacgctc gcgctgttcg gcaccggcac ggtgatggtc    900

aaccgcggtt cgggccagaa cgacggggtc gtgtcgaagt gcagcgcgct gtacggccag    960

gtgctgagca cgagctacaa gtggaaccat ctcgacgaga tcaaccagtt gctcggcgtg   1020

cgcggcgcga atgcggaaga tccggtcgcg gtgatccgca cgcatgcgaa ccggctgaag   1080

ctcgcgggcg tgtga                                                     1095
```

<210> SEQ ID NO 16
<211> LENGTH: 1095
<212> TYPE: DNA
<213> ORGANISM: Artificial Sequence
<220> FEATURE:
<223> OTHER INFORMATION: DNA coding a mutant Q88M of lipase from
      Burkholderia cepacia

<400> SEQUENCE: 16

```
atggccagat cgatgcgttc cagggtggtg gcaggggcag tggcatgcgc gatgagcgtc     60

gcgccgttcg cggggatgac cgcggcgatg acgctcgcga cgacgcgcgc ggcaatggcg    120

gcgagcgcgc ccgccgacaa ctacgcggcg acgcgttatc cgatcattct cgtgcacggg    180
```

-continued

```
ctcacgggca ccgacaaata cgcaggtgtg ctcgagtact ggtacgggat ccaggaggac    240

ctgcagcagc gtggcgcgac cgtctatgtc gctaacctgt cgggcttcca gagcgacgac    300

ggcccgaacg ggcgcggcga acagttgctg gcctacgtga agacggtgct cgccgcgacg    360

ggggcgacca aggtcaacct cgtcggccac agcatgggcg ggctgacgtc gcgctatgtc    420

gcggccgtcg cgcccgatct ggtcgcgtcg gtgacgacga tcggcacgcc gcatcgcggc    480

tccgagttcg ccgacttcgt gcagggcgtg ctcgcgtacg atccgaccgg gctgtcgtcg    540

acggtgatcg ccgcgttcgt caatgtgttc ggaatcctca cgagcagcag caacaacacg    600

aaccaggacg cgctcgcggc gctgaagacg ctgacgaccg cgcaggccgc cacgtacaac    660

cagaactacc ctagcgcggg cctcggcgcg ccgggcagtt gccagaccgg cgcgccgacg    720

gaaaccgtcg gcggcaacac gcatctgctg tattcgtggg ccggcacggc gatccagccg    780

acgatctccg tgttcggcgt cacgggtgcg acggatacga gcaccattcc gctcgtcgat    840

ccggcgaacg cgctcgaccc gtcgacgctc gcgctgttcg gcaccggcac ggtgatggtc    900

aaccgcggtt cgggccagaa cgacggggtc gtgtcgaagt gcagcgcgct gtacggccag    960

gtgctgagca cgagctacaa gtggaaccat ctcgacgaga tcaaccagtt gctcggcgtg   1020

cgcggcgcga atgcggaaga tccggtcgcg gtgatccgca cgcatgcgaa ccggctgaag   1080

ctcgcgggcg tgtga                                                    1095
```

<210> SEQ ID NO 17
<211> LENGTH: 1095
<212> TYPE: DNA
<213> ORGANISM: Artificial Sequence
<220> FEATURE:
<223> OTHER INFORMATION: DNA coding a mutant Q88L of lipase from
      Burkholderia cepacia

<400> SEQUENCE: 17

```
atggccagat cgatgcgttc cagggtggtg gcaggggcag tggcatgcgc gatgagcgtc     60

gcgccgttcg cggggatgac cgcggcgatg acgctcgcga cgacgcgcgc ggcaatggcg    120

gcgagcgcgc ccgccgacaa ctacgcggcg acgcgttatc cgatcattct cgtgcacggg    180

ctcacgggca ccgacaaata cgcaggtgtg ctcgagtact ggtacgggat ccaggaggac    240

ctgcagcagc gtggcgcgac cgtctatgtc gctaacctgt cgggcttcca gagcgacgac    300

ggcccgaacg ggcgcggcga acagttgctg gcctacgtga agacggtgct cgccgcgacg    360

ggggcgacca aggtcaacct cgtcggccac agcctgggcg ggctgacgtc gcgctatgtc    420

gcggccgtcg cgcccgatct ggtcgcgtcg gtgacgacga tcggcacgcc gcatcgcggc    480

tccgagttcg ccgacttcgt gcagggcgtg ctcgcgtacg atccgaccgg gctgtcgtcg    540

acggtgatcg ccgcgttcgt caatgtgttc ggaatcctca cgagcagcag caacaacacg    600

aaccaggacg cgctcgcggc gctgaagacg ctgacgaccg cgcaggccgc cacgtacaac    660

cagaactacc ctagcgcggg cctcggcgcg ccgggcagtt gccagaccgg cgcgccgacg    720

gaaaccgtcg gcggcaacac gcatctgctg tattcgtggg ccggcacggc gatccagccg    780

acgatctccg tgttcggcgt cacgggtgcg acggatacga gcaccattcc gctcgtcgat    840

ccggcgaacg cgctcgaccc gtcgacgctc gcgctgttcg gcaccggcac ggtgatggtc    900

aaccgcggtt cgggccagaa cgacggggtc gtgtcgaagt gcagcgcgct gtacggccag    960
```

-continued

```
gtgctgagca cgagctacaa gtggaaccat ctcgacgaga tcaaccagtt gctcggcgtg   1020

cgcggcgcga atgcggaaga tccggtcgcg gtgatccgca cgcatgcgaa ccggctgaag   1080

ctcgcgggcg tgtga                                                    1095
```